United States Patent
Lu et al.

(10) Patent No.: US 12,151,012 B2
(45) Date of Patent: Nov. 26, 2024

(54) GEL TEXTURIZER BASE FOR COSMETICS

(71) Applicant: Juice Beauty, Inc., San Rafael, CA (US)

(72) Inventors: Mimi Lu, San Rafael, CA (US); Karen Behnke, San Rafael, CA (US)

(73) Assignee: Juice Beauty, Inc., San Rafael, CA (US)

( * ) Notice: Subject to any disclaimer, the term of this patent is extended or adjusted under 35 U.S.C. 154(b) by 0 days.

(21) Appl. No.: 17/719,283

(22) Filed: Apr. 12, 2022

(65) Prior Publication Data

US 2022/0233426 A1 Jul. 28, 2022

Related U.S. Application Data

(63) Continuation of application No. 16/578,040, filed on Sep. 20, 2019, now abandoned.

(60) Provisional application No. 62/734,790, filed on Sep. 21, 2018.

(51) Int. Cl.
| | |
|---|---|
| *A61K 8/73* | (2006.01) |
| *A61K 8/04* | (2006.01) |
| *A61K 8/25* | (2006.01) |
| *A61K 8/26* | (2006.01) |
| *A61K 8/31* | (2006.01) |
| *A61K 8/34* | (2006.01) |
| *A61K 8/365* | (2006.01) |
| *A61K 8/37* | (2006.01) |
| *A61K 8/49* | (2006.01) |
| *A61K 8/58* | (2006.01) |
| *A61K 8/67* | (2006.01) |
| *A61K 8/89* | (2006.01) |
| *A61K 8/891* | (2006.01) |
| *A61K 8/92* | (2006.01) |
| *A61K 8/9789* | (2017.01) |
| *A61K 8/9794* | (2017.01) |
| *A61Q 19/00* | (2006.01) |

(52) U.S. Cl.
CPC ............... *A61K 8/73* (2013.01); *A61K 8/042* (2013.01); *A61K 8/25* (2013.01); *A61K 8/26* (2013.01); *A61K 8/31* (2013.01); *A61K 8/345* (2013.01); *A61K 8/365* (2013.01); *A61K 8/37* (2013.01); *A61K 8/375* (2013.01); *A61K 8/498* (2013.01); *A61K 8/585* (2013.01); *A61K 8/678* (2013.01); *A61K 8/89* (2013.01); *A61K 8/891* (2013.01); *A61K 8/922* (2013.01); *A61K 8/9789* (2017.08); *A61K 8/9794* (2017.08); *A61Q 19/00* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 4,481,185 | A | 11/1984 | Grollier et al. |
| 5,994,414 | A | 11/1999 | Franco et al. |
| 2005/0089499 | A1 | 4/2005 | Moussou et al. |
| 2005/0281853 | A1 | 12/2005 | Fox et al. |
| 2019/0192390 | A1 | 6/2019 | Lu et al. |

FOREIGN PATENT DOCUMENTS

WO 2007053815 A2 5/2007

OTHER PUBLICATIONS

Juice Beauty "Prebiotix Hydrating Gel Moisturizer"—product data sheet obtained from the website: https://www.ulta.com/p/prebiotix-hydrating-gel-moisturizer-pimprod2002001. (Year: 2018).*
"All About Sunflower" (an internet article published on Jun. 19, 2018, obtained from the website: https://www.newdirectionsaromatics.com/blog/products/all-about-sunflower-oil.html). (Year: 2018).*
Hassan( "Vitamin E in dermatology" Indian Dermatol Online J. vol.7(4) (Jul.-Aug. 2016), p. 311-315). (Year: 2016).*
INCIDecoder product sheet for Juice Beauty's "Prebiotix Hydrating Gel Moisturizer" obtained from the website: https://incidecoder.com/products/juice-beauty-prebiotix-hydrating-gel-moisturizer (dated Jan. 8, 2019).*
Reflection of Sanity ("Your Summer Best Friend Ft. Juice Beauty Prebiotix Hydrating Gel Moisturizer" an internet blog review article obtained from https://www.reflectionofsanity.com/2019/04/ (dated Apr. 1, 2019).*
Reflection of Sanity ("Your Summer Best Friend Ft. Juice Beauty Prebiotix Hydrating Gel Moisturizer" an internet blog review article obtained from https://www.reflectionofsanity.com/2019/04/your-summer-best-friend-ft-juice-beauty.html#more (dated Apr. 1, 2019).*
"Distinctive® Emul-Lipid BA", Resources of Nature, Inc., Dec. 31, 2013, 5 pages.
"Prebiotix Hydrating Gel Moisturizer", Juice Beauty, Available Online At: https://incidecoder.com/products/juice-beauty-prebiotix-hydrating-gel-moisturizer, Jan. 2019, 6 pages.
U.S. Appl. No. 16/578,040, Non-Final Office Action, Mailed on Nov. 12, 2021, 10 pages.
Gilbert et al., "Impact of Polymers on Texture Properties of Cosmetic Emulsions: A Methodological Approach", Journal of Sensory Studies, vol. 27, Oct. 5, 2012, pp. 392-402.

* cited by examiner

*Primary Examiner* — Sin J Lee
(74) *Attorney, Agent, or Firm* — Nixon Peabody LLP; Elizabeth Baio; Nicole D. Kling

(57) ABSTRACT

This invention provides for a gel texturizer base for cosmetic products. The bases are excipients that provide a gel-like texture to cosmetic products. The gel texturizer bases of this invention are from non-petroleum based products and comprise over 85% juice derived solvent with the balance being a combination of a texture enhancer and a gum texture modifier.

26 Claims, No Drawings

GEL TEXTURIZER BASE FOR COSMETICS

CROSS-REFERENCE TO RELATED APPLICATIONS

The present application is a continuation of Non-provisional patent application Ser. No. 16/578,040 filed Sep. 20, 2019, and claims the benefit of priority to U.S. Provisional Application No. 62/734,790, filed Sep. 21, 2018, the full disclosure of which is incorporated herein by reference in its entirety for all purposes.

BACKGROUND OF THE INVENTION

There are hundreds of skin care products on the market today designed to provide a variety of benefits and care for hands, feet, body, eyes, face, etc. Texturizing agents represent an important sector of so-called cosmetic products because they in fact constitute the vehicles for numerous formulations such as moisturizers, cleansers, facial serums and masks, make-up, foundation, topical facial medications and the like. These gel-based cosmetic compositions are obtained by using structuring polymers and viscous gelling agents by means of which three-dimensional networks are produced. Because these gel formulations can be unstable, they can eventually, given enough time or energy, separate and/or exhibit syneresis.

Consequently, many gel texturizer base systems are comprised of synthetic or semi-synthetic materials. However, skin care products which contain such synthetic materials in gel texturizers vary in effectiveness, and, in addition to being ineffective, many of them can have adverse side effects and can even damage the skin. Unfortunately, few natural gel texturizers are capable of giving gels which at one and the same time exhibit desirable tactile properties, texture attributes, and appearance as well as good stability. There is a need for gel texturizer bases made of naturally occurring and non-synthetic components for cosmetic products. The present invention solves these problems and more by providing a gel texturizer base, comprising a plant juice solvent, texture enhancer, and a gum texture modifier.

BRIEF SUMMARY OF THE INVENTION

In one aspect, the present invention provides a non-petroleum based gel texturizer base for cosmetic products comprising a solvent, a texture enhancer, and a gum texture modifier. The solvent is a plant juice derived supernatant having about 6.0 to about 20.0% carbohydrate content and an acidic pH of between about 2.2 and about 6.0, wherein the amount of the solvent ranges from about 89.0 to 94.0% of the total weight of the gel texturizer base. The texture enhancer is a mixture consisting essentially of about 87.0 to 92.0% coconut alkanes, about 4.0 to 6.5% coco-caprylate/caprate, about 1.5 to 3.5% bio-silicate fermentation product, and about 1.5 to 3.5% polysaccharide conditioner, wherein the amount of the texture enhancer ranges from about 2.0 to 5.0% of the total weight of the gel texturizer base. The gum texture modifier is a mixture consisting essentially of about 44.5 to 53.0% clay, about 19.5 to 25.0% polysaccharide thickener, about 2.8 to 6.0% polysaccharide stabilizer, and about 21.5 to 28.0% glyceryl stearate, wherein the amount of the gum texture modifier ranges from about 4.0 to 6.5% of the total weight of the gel texturizer base. The weight to weight ratio of the texture enhancer to the gum texture modifier of the gel texturizer base ranges from 0.35 to 0.75.

In some embodiments, the invention provides a gel texturizer base, wherein the solvent is a plant juice selected from the group consisting of aloe, grape, lemon, apple, and mixtures thereof. In some embodiments, the solvent is a plant juice mixture consisting of aloe, grape, and apple. In some embodiments, the solvent of the gel texturizer base has a pH of between about 3.0 and about 5.0. In some embodiments, the invention provides a gel texturizer base, wherein the texture enhancer consists of coconut alkanes that is about 85.0 to about 90.0% C12 alkanes. In some embodiments, the weight to weight ratio of the bio-silicate fermentation product to the polysaccharide conditioner ranges from 0.9 to 1.1.

In some embodiments, the bio-silicate fermentation product is derived from leaves and stalks of bamboo. In some embodiments, the polysaccharide conditioner is biosaccharide gum. In some embodiments, the clay is smectite clay. In some embodiments, the smectite clay is selected from the group consisting of montmorillonites, hectorites, bentonites, attapulgites, sepiolites, beidellites, saponites, and mixtures thereof. In some embodiments, the polysaccharide thickener is xanthan gum. In some embodiments, the polysaccharide stabilizer is a sulfated galactose-based polysaccharide. In some embodiments, the sulfated galactose-based polysaccharide is carrageenan.

In a related aspect, the invention provides a composition comprising the gel texturizer base as described herein and a fresh fragrance. In some embodiments, the fresh fragrance of the gel texturizer base composition described herein is a blend of any two or more pure essential oils selected from the group consisting of may chang oil, ylang ylang oil, bergamot oil, frankincense oil, lavender oil, orange peel oil, juniper oil, and clary sage oil. In another aspect, the invention provides a moisturizing composition comprising the gel texturizer base as described herein and at least one compound selected from the group consisting of caprylic/capric triglyceride, cyclomethicone, dimethicone, glycols, hyaluronic acid, fragrance, polymers, and peptides. In some embodiments, the moisturizing composition comprising the gel texturizer base as described herein has a pH of between about 5.0 and about 6.5. In some embodiments, the moisturizing composition comprising the gel texturizer base as described herein has a viscosity of between about 180,000 and 600,000 cP. In some embodiments, the moisturizing composition comprising the gel texturizer base as described herein has a specific gravity of between 0.99 to 1.1 and wherein the density ratio is in comparison to water at 4° C. and 1 atm. In some embodiments, the moisturizing composition comprising the gel texturizer base as described herein is a cosmetic product comprising about 55.0 to about 78.0% of the solvent, about 1.0 to about 4.0% of the texture enhancer, and about 1.5 to about 5.5% of the gum texture modifier.

In another related aspect, the invention provides an eye treatment composition comprising the gel texturizer base as described herein and at least one compound selected from the group consisting of peptides, plant butters, silicones, and polymers. In yet another related aspect, the invention provides a facial mask composition comprising the gel texturizer base as described herein and at least one compound selected from the group consisting of kaolin, glycerin, dimethicone, PEGs, polysorbate, plant extracts, and magnesium silicate. In a further related aspect, the invention provides a composition comprising the gel texturizer base as described herein and sunflower seed oil and/or tocopherol. In a further related aspect, the invention provides a composition comprising the gel texturizer base as described herein and alpha-hydroxy acids, beta-hydroxy acids, or a combination thereof.

In another aspect, the present invention provides a method of manufacturing a non-petroleum based gel texturizer base for cosmetic products by combining a solvent, a texture enhancer, and a gum texture modifier. The solvent is a plant juice derived supernatant having about 6.0 to about 20.0% carbohydrate content and an acidic pH of between about 2.2 and about 6.0, wherein the amount of the solvent ranges from about 89.0 to 94.0% of the total weight of the gel texturizer base. The texture enhancer is a mixture consisting essentially of about 87.0 to 92.0% coconut alkanes, about 4.0 to 6.5% coco-caprylate/caprate, about 1.5 to 3.5% biosilicate fermentation product, and about 1.5 to 3.5% polysaccharide conditioner, wherein the amount of the texture enhancer ranges from about 2.0 to 5.0% of the total weight of the gel texturizer base. The gum texture modifier is a mixture consisting essentially of about 44.5 to 53.0% clay, about 19.5 to 25.0% polysaccharide thickener, about 2.8 to 6.0% polysaccharide stabilizer, and about 21.5 to 28.0% glyceryl stearate, wherein the amount of the gum texture modifier ranges from about 4.0 to 6.5% of the total weight of the gel texturizer base. The weight to weight ratio of the texture enhancer to the gum texture modifier of the gel texturizer base ranges from 0.35 to 0.75.

DETAILED DESCRIPTION OF THE INVENTION

I. INTRODUCTION

This invention provides for a gel texturizer base for cosmetic products having low to medium viscosity. Such bases are excipients that provide a gel-like texture to cosmetic products. The gel texturizer bases of this invention are from non-petroleum based products and comprise over 85% juice derived solvent and up to 15% of a texture enhancer and gum texture modifier mixture. A key feature of this invention is the ratio of the texture enhancer to the gum texture modifier which provides the necessary texture and required after feel and appearance properties.

Using organic juices as a base composition for a skin care product is a costly process with many challenging logistics. For example, seasonal produce, weather sensitivity and the fact that each crop has unique chemistry and colors combine to make the development of juice-based organic skin care products extremely difficult. Implementing a juice-based solvent gel texturizer composition is exceedingly more difficult given the inherent instability of gel texturizer systems having the desired sensorial properties. However, the juice-containing gel texturizer bases described herein prove to exhibit stability and desired tactile sensations.

Organic juices are rich in potent antioxidants, essential vitamins, vital phytonutrients, and powerful hydroxy acids, making them excellent ingredients for skin care products. The gel texturizer base compositions below do not make use of artificial fillers, toxic preservatives, water to dilute the compositions, tars, petroleum, synthetic fragrances, or parabens.

II. DEFINITIONS

The term "texture enhancer" refers to a homogeneous four-component mixture of occlusive-like additives, which include non-polar oils, polar oils, and natural fermented lubricants, which is used to produce gel texturizer bases with the solvent and the gum texture modifier. Thus, the texture enhancer provides an observable or otherwise detectable improvement in the tactile sensation experienced by touching and/or feeling the gel texturizer base, compared to a gel texturizer base that does not contain the texture enhancer component. Texture enhancer compounds/compositions are described in detail in the present application.

"Non-polar" oils are generally oils which are hydrocarbons ("alkanes") and are more hydrophobic and lipophilic compared to synthetic oils, such as esters, which may be referred to as "polar" oils. It is understood that within the class of oils, that the use of the terms "non-polar" and "polar" are relative within this very hydrophobic and lipophilic class, and all of the oils tend to be much more hydrophobic and lipophilic than the "solvent" which is used in the gel texturizer base of the present invention.

The terms "alkane" and "alkanes" refer to non-aromatic, saturated hydrocarbons with the general formula $C_nH_{(2n+2)}$, wherein n is an integer from, for example, 10 to 22, preferably 12 to 18. The alkanes can exist as a mixture of linear and branched saturated hydrocarbons. Alkanes particularly useful for the alkane texture enhancer of the instant invention, for example, are liquid at room temperature (i.e., 20° C. to 25.5° C.) and are alkanes having 12 and 14 carbons (i.e., C12 and C14, respectively).

The term "fresh fragrance" refers to any odoriferous mixture of essential oils which provides the gel texturizer base and/or cosmetic product compositions comprising the gel texturizer base described herein with a pleasing fresh and light odor. Fresh and light fragrances are typically those perceived as non-sweet with a predominant fresh note that is often associated with citrus, greens or aldehydes. The fresh fragrance can include one or two components. Examples of fresh fragrances include, but are not limited to, may chang oil, ylang ylang oil, bergamot oil, frankincense oil, lavender oil, orange peel oil, juniper oil, clary sage oil, and combinations thereof.

The term "gum texture modifier" refers to a homogeneous three-component mixture of rheological, thickening additives, which include natural and inorganic compounds, used to produce gel texturizer bases with the solvent and the texture enhancer. The components of the gum texture modifier impart viscosity, elasticity, stability, and suspending power to the gel texturizer bases of the invention by increasing the interaction between the hydrophilic continuous phase (i.e., the solvent) and the lipophilic internal phase (i.e., the texture enhancer). Gum texture modifier compounds/compositions are described in detail in the present application.

The terms "plant juice" and "plant juice derived supernatant" refer to the aqueous-based liquid that is obtained from any suitable plant or part thereof. Plant juice is the solvent component of the gel texturizer base of the invention.

The term "percent weight," unless otherwise defined, means % or refers to the percentage of a component measured in weight per total weight of a particular composition. Percent weight is represented by "%" or "% w/w."

The terms "peptide(s)," "polypeptide(s)," and "protein(s)" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds. Such amino acid polymers can be incorporated into the cosmetic products described herein which comprise the gel texturizer base of the instant invention.

The term "solvent" refers to the aqueous mixture derived from plant juice and can be used to produce gel texturizer bases with the texture enhancer and the gum texture modifier. Solvent compositions are described in detail in the present application.

The phrase "gel texturizer base" refers to the base excipient formulated alongside the active ingredients of a cosmetic product. The gel texturizer base is typically inert and present for the purpose of providing a gel-like texture to the whole cosmetic product, such as, for example, moisturizing compositions, eye treatment compositions, and facial mask compositions. The solvent, the texture enhancer, and the gum texture modifier are the three components of the gel texturizer base. Gel texturizer base compositions are described in detail in the present application.

The terms "gel" or "gel-like" are used to define the physical-chemical properties and structural matrix of the gel texture base compositions of the instant invention as a semisolid disperse system of at least two constituents, consisting of a condensed mass enclosing and interpenetrated by a liquid. The physical state of a gel is formed by a network of interconnected molecules and liquid, in which both the network of molecules is continuous and the liquid is continuous, such as a cross-linked polymer or a network of micelles. The network gives a gel phase its structure. At the molecular level, a gel is a type of disperse system and sometimes considered as a single phase having a self-sustaining structure which does not require physical or external support (i.e., can hold a shape) for a given period of time at constant temperature, for example, from the time of preparation to the time of application or end use. These terms can also mean that the composition is not easily pourable.

Technically, a gel is a semi-solid, jelly-like physical state or phase that can have properties ranging from soft and weak to hard and tough. Shearing stresses below a certain finite value fail to produce permanent deformation. The minimum shear stress which will produce permanent deformation is referred to as the shear strength or gel strength of the gel. In other words, the gel-like structure of the texturizing base compositions of the invention is hard or rigid enough such that a sufficient amount of pressure or force applied on the structure is required in order to break the structure. For example, a shearing force or a pressing action with the hands or fingers can be used in order to distribute the formula in the hand or onto a surface, such as the surface of facial skin.

Viscoelasticity is the property of materials that exhibit both viscous and elastic characteristics when undergoing deformation. Viscous materials resist shear flow and strain linearly with time when a stress is applied. Elastic materials strain when stretched and quickly return to their original state once the stress is removed. Viscoelastic materials have elements of both of these properties and, as such, exhibit time-dependent strain. Thus, the term "viscoelastic" as used herein with respect to the gel texturizer base of the present disclosure, and components thereof, refers to the ability of the gel texturizing agents, and compositions thereof, to change shape when a certain amount of pressure or force is applied to the compositions, as well as return to the original shape when the pressure or force is removed. Said amount of pressure or force is such that it is not sufficient to break the gel structure of the compositions of the invention.

The phrase "non-petroleum based" refers to ingredients of the gel texturizer base for which crude oil or its derivatives are not the ultimate raw material (i.e., starting material). An exemplary non-petroleum resource includes, but is not limited to, bio-based resources, such as those derived from plains.

The terms "essential oil" or "essential oils" refer to aromatic, volatile liquids extracted from plant material. Essential oils are often concentrated hydrophobic liquids containing volatile aroma compounds. Essential oil chemical constituents can fall within general classes, such as terpenes (e.g., p-cymene, limonene, sabinene, α-pinene, γ-terpinene, β-caryophyllene), terpenoids (e.g., citronellal, thymol, carvacrol, carvone, borneol) and phenylpropanoids (e.g., cinnamaldehyde, eugenol, vanillin, safrole). Essential oils can be natural (i.e., derived from plants).

The terms "pure" or "substantially pure" refer to an object species (e.g., a particular essential oil) is the predominant species present (i.e., on a molar basis it is more abundant than any other essential oil in the composition thereof), and preferably a substantially purified fraction is a composition wherein the object species comprises at least about 50 percent (on a molar basis) of all macromolecular species present. Generally, a substantially pure composition (e.g., an essential oil or blend of essential oils) will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species. The term "pure" or "substantially pure" also refers to preparations where the object species (e.g., the essential oil) is at least 60% (w/w) pure, or at least 70% (w/w) pure; or at least 75% (w/w) pure; or at least 80% (w/w) pure; or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

III. GEL TEXTURIZER BASE COMPONENTS

Solvents

The solvent component of the non-petroleum based gel texturizer base of the instant invention is a plant juice, which acts as a continuous hydrophilic and aqueous phase of the dispersion system matrix (i.e., the gel texturizer base) throughout which the texture enhancer and gum texture modifier are dispersed. In addition to being the main constituent of the gel texturizer base composition, the solvent provides a high load of antioxidant rich nutrients to any cosmetic product that contains the gel texturizer base of the invention.

Any suitable plant juice is useful as a solvent in the gel texturizer base, such as, for example, *Aloe barbadensis* leaf juice (aloe), *Vitis vinifera* juice (grape), *Pyrus malus* juice (apple), *Citrus limon* juice (lemon), *Citrus aurantium* juice (orange), and mixtures thereof. Preferably the solvent is derived from certified organic fruit or plants. Various parts of the plants (i.e., plant biomass) may be used as the solvent. For example, the stems and leaf tissue may be used for many types of plants. For other plants, the flowers or fruit may be used as sources of plant juice for use in the present invention. For example, the fruit tissue of grape, apple, or lemon can be used to obtain the solvent as the plant juice derived supernatant. In another embodiment, the leaf and stem tissue of the aloe plant can be used to obtain the solvent as the plant juice derived supernatant.

The solvent (i.e., the plant juice derived supernatant) can be obtained using suitable extracting methods known in the art. However, the extraction technique should result in a plant juice that preserves the bioactive components of the plant. An exemplary method of obtaining the plant juice derived supernatant involves harvesting the suitable plant biomass (i.e., fruit, flower, leaf, stem, etc.), preparing the harvested biomass for the extraction process, and extraction.

The plant biomass should be harvested in conditions which avoid moisture loss of the plant biomass. Optimal conditions are those where natural moisture content is maintained and preserved. Harvesting of the plant biomass may be conducted in a manner that avoids or minimizes the chopping, mashing, crushing, or other type of injury of the plant. Delivery time of plant material to the processing facility and exposure of biomass to sun, high temperature, and other negative environmental factors, should be minimized to prevent the impact of unwanted degradation processes. The harvested plant mass should be washed remove the soil particles and other debris from plants prior to grinding and maceration once the plant tissue is harvested.

After the plant biomass is harvested, as described above, the plant biomass is subjected to grinding, maceration, and pressing to extract the intracellular content (i.e., the plant juice derived supernatant, and to separate it from the fiber-enriched press-cake containing predominantly cell walls). For example, a hammer mill may be used to grind the plant biomass to yield plant tissue particles of a small size in a short time and without significant increase of biomass temperature. In one embodiment, a modified hammer mill is used to produce the maximum size of macerated plant particles less than or equal to 0.5 centimeters during less than or equal to 10 seconds of treatment, where the increase of biomass temperature is less than or equal to 5° C. The extraction of the plant juice and its separation from the press-cake is commenced as soon as possible after grinding and maceration of the plant biomass. The plant biomass is processed in a short time and without significant increase in temperature. In one embodiment, immediately after grinding and maceration, the plant biomass is pressed using a horizontal, continuous screw press (Compact Press "CP-6", Vincent Corporation, FL). The pressure on the cone is maintained at level 24 kg/cm$^2$, screw speed is at 12 rpm, and the temperature increase is less than or equal to 5° C.

The initial plant juice supernatant usually contains small fiber particles, which can absorb valuable plant juice components and also block the hoses and pumps of dispensers. The above particles should be removed by filtration or low-speed centrifugation. For example, the initial plant juices produced after the pressing step are filtered through four layers of nylon fabric. The filtrate, or the plant juice derived supernatant, is collected and used as the solvent. In some embodiments, a suitable solvent for use in the gel texturizer base may optionally be prepared from a concentrated extracted plant juice or filtrate according to applicable government guidelines. In some cases, suitable plant juice derived supernatants used as the solvent in the gel texturizer base of the invention are commercially available and can be purchased from, for example, Jedwards International, Inc. (Braintree, MA), Concentrated Aloe Corporation (Ormond Beach, FL), Aloecorp, Inc. (Tacoma, WA), and Charkit Chemical Company LLC (Norwalk, CT).

The plant juice derived supernatant (i.e., solvent) will have a carbohydrate content that is between about 6.0% and 20.0% of the solvent. In some embodiments, the plant juice will have a carbohydrate content that is between about 6.0% and about 10.0%, about 8.0% and about 18.0%, about 10.0% and about 16.0%, or about 12.0% and about 16.0% of the solvent. In some embodiments, the plant juice will have a carbohydrate content that is about 7.0%, about 11.0%, or about 17%. The carbohydrate content of the plant juice derived supernatant can be measured by any of many analytical methods available in the field and well known to one of skill in the art, such as, for example, high performance chromatography (HPLC), gas chromatography (GC), colorimetric methods, gravimetric methods (e.g., using hydrometers), refractometers, electric tongue, visible infrared spectroscopy, near infrared spectroscopy, hyperspectral imaging, multispectral imaging, or combinations thereof. See, Magwaza, L. S. et al. 2015 *Scientia Horticulturae*, (184) 179-192.

The plant juice solvent will have an acidic pH that is between about 2.2 and about 6.0. In some embodiments, the plant juice will have an acidic pH that is between about 2.5 and about 5.5, about 3.0 and about 5.0, or about 3.5 and about 4.5. In some embodiments, the plant juice will have an acidic pH that is between about 4.0 and about 5.0. In other embodiments, the plant juice will have an acidic pH that is about 2.5 or 3.6.

In some embodiments, the solvent used in the gel texturizer base of the present invention can have a bacterial cell count (i.e., aerobic plate count, "APC") of less than 150 CFU/g (colony forming units per gram of solvent). For example, the bacterial cell count of the plant juice derived supernatant can be between about 0 CFU/g and about 145 CFU/g, between about 30 CFU/g and about 120 CFU/g, or between about 50 CFU/g and about 100 CFU/g. In some embodiments, the plant juice solvent will have a bacterial cell count that is less than 150 CFU/g, less than 100 CFU/g, or less than 50 CFU/g. In some embodiments, the solvent has a bacterial cell count that is less than 150 CFU/g. In some embodiments, the solvent has a bacterial cell count that is less than 100 CFU/g. In some embodiments, the solvent has a bacterial cell count that is less than 50 CFU/g.

A culture-based method can be used to determine the bacterial cell count of the solvent, in which serial dilutions of the plant juice cultures are plated onto agar plates containing the appropriate nutrients and incubated for about 48 hour aerobically at mesophilic temperatures (25 to 40° C., or 35° C., for example). Colonies on the plates are counted and the number of CFUs (colony forming units) in the samples are calculated as CFU/mL or CFU/gram. Methods of determining the CFUs are described in detail below.

In some embodiments, the solvent is aloe plant juice, grape juice, lemon juice, apple juice, or orange juice. In some embodiments, the solvent is aloe plant juice, grape juice, lemon juice, or apple juice. In some embodiments, the solvent is aloe plant juice. In some embodiments, the solvent is grape juice. In some embodiments, the solvent is lemon juice. In some embodiments, the solvent is apple juice. In some embodiments, the solvent is orange juice. In some embodiments, the solvent is a plant juice mixture of two or more plant juices selected from aloe plant juice, grape juice, lemon juice, apple juice, and orange juice. In some embodiments, the solvent is a plant juice mixture of two or more plant juices selected from aloe plant juice, grape juice, lemon juice, and apple juice. In other embodiments, the solvent is a plant juice mixture of two or more plant juices selected from aloe plant juice, apple juice, and grape juice. In some embodiments, the solvent is a plant juice mixture consisting of aloe plant juice, apple juice, and grape juice.

In some embodiments, the solvent is a plant juice mixture consisting of any suitable amounts of aloe plant juice, apple juice, and grape juice. For example, the plant juice mixture may comprise from about 50.0 to 75.0% aloe plant juice, from about 15.0 to 30.0% apple juice, and from about 10.0 to 20.0% grape juice. In some embodiments, the plant juice mixture is from about 55.0 to 70.0% aloe plant juice, from about 18.0 to 28.0% apple juice, and from about 12.0 to 18.0% grape juice. In other embodiments, the plant juice mixture is from about 60.0 to 65.0% aloe plant juice, from about 20.0 to 25.0% apple juice, and from about 12.0 to 18.0% grape juice. In other embodiments, the plant juice mixture is about 60.0 to 63.0% aloe plant juice, about 20.0 to 23.0% apple juice, and about 13.0 to 16.0% grape juice.

In some embodiments, the solvent is an aloe plant juice derived supernatant having a carbohydrate content of about 6.0 to about 20.0% and an acidic pH of between about 2.2 and about 6.0. In some embodiments, the solvent is an aloe plant juice derived supernatant having a carbohydrate content of about 11.3% and an acidic pH of between about 3.0 and about 5.0. In some embodiments, the solvent is a grape juice derived supernatant having a carbohydrate content of about 6.0 to about 20.0% and an acidic pH of between about 2.2 and about 6.0. In some embodiments, the solvent is a grape juice derived supernatant having a carbohydrate content of about 17.4% and an acidic pH of between about 4.0 and about 5.0. In some embodiments, the solvent is an apple juice derived supernatant having a carbohydrate content of about 6.0 to about 20.0% and an acidic pH of between about 2.2 and about 6.0. In some embodiments, the solvent is an apple juice derived supernatant having a carbohydrate content of about 11.2% and an acidic pH of about 3.6. In some embodiments, the solvent is a lemon juice derived supernatant having a carbohydrate content of about 6.0 to 10.0% and an acidic pH of between about 2.2 and about 6.0. In some embodiments, the solvent is a lemon juice derived supernatant having a carbohydrate content of about 7.0% and an acidic pH of about 2.5.

In some embodiments, the solvent is a plant juice mixture having a carbohydrate content of about 6.0 to 20.0% and an acidic pH of between about 2.2 and about 6.0. In some embodiments, the solvent is a plant juice mixture having a carbohydrate content of about 12.0 to 15.0% and an acidic pH of between about 3.0 and about 5.0. In some embodiments, the solvent is a plant juice mixture consisting of aloe plant juice, apple juice, and grape juice, having a carbohydrate content of about 6.0 to 20.0% and an acidic pH of about 2.2 and about 6.0. In some embodiments, the solvent is a plant juice mixture consisting of aloe plant juice, apple juice, and grape juice, having a carbohydrate content of about 12.0 to 15.0% and an acidic pH of between about 3.0 and about 5.0.

In some embodiments, the solvent is an aloe plant juice derived supernatant having a carbohydrate content of 6.0 to about 20.0%, an acidic pH of between about 2.2 and about 6.0, and a bacterial cell count of less than 150 CFU/g. In some embodiments, the solvent is an aloe plant juice derived supernatant having a carbohydrate content of about 11.3%, an acidic pH of between about 3.0 and about 5.0, and a bacterial cell count of less than 150 CFU/g. In some embodiments, the solvent is a grape juice derived supernatant having a carbohydrate content of 6.0 to about 20.0%, an acidic pH of between about 2.2 and about 6.0, and a bacterial cell count of less than 150 CFU/g. In some embodiments, the solvent is a grape juice derived supernatant having a carbohydrate content of about 17.4%, an acidic pH of between about 4.0 and about 5.0, and a bacterial cell count of less than 150 CFU/g. In some embodiments, the solvent is an apple juice derived supernatant having a carbohydrate content of about 6.0 to about 20.0%, an acidic pH of between about 2.2 and about 6.0, and a bacterial cell count of less than 150 CFU/g. In some embodiments, the solvent is an apple juice derived supernatant having a carbohydrate content of about 11.2%, an acidic pH of about 3.6, and a bacterial cell count of less than 150 CFU/g. In some embodiments, the solvent is a lemon juice derived supernatant having a carbohydrate content of about 6.0 to 10.0%, an acidic pH of between about 2.2 and about 6.0, and a bacterial cell count of less than 150 CFU/g. In some embodiments, the solvent is a lemon juice derived supernatant having a carbohydrate content of about 7.0%, an acidic pH of about 2.5, and a bacterial cell count of less than 150 CFU/g.

In some embodiments, the solvent is a plant juice mixture having a carbohydrate content of about 6.0 to 20.0%, an acidic pH of between about 2.2 and about 6.0, and a bacterial cell count of less than 150 CFU/g. In some embodiments, the solvent is a plant juice mixture having a carbohydrate content of about 12.0 to 15.0%, an acidic pH of between about 3.0 and about 5.0, and a bacterial cell count of less than 150 CFU/g. In some embodiments, the solvent is a plant juice mixture consisting of aloe plant juice, apple juice, and grape juice, having a carbohydrate content of about 6.0 to 20.0%, an acidic pH of between about 2.2 and about 6.0, and a bacterial cell count of less than 150 CFU/g. In some embodiments, the solvent is a plant juice mixture consisting of aloe plant juice, apple juice, and grape juice, having a carbohydrate content of about 12.0 to 15.0%, an acidic pH of between about 3.0 and about 5.0, and a bacterial cell count of less than 150 CFU/g.

Texture Enhancers

The texture enhancer component of the gel texturizer base of the invention is the lipophilic internal phase of the gel dispersion system. The texture enhancer is a smooth, occlusive liquid that is a pale yellow color. The constituents of the texture enhancer of the gel texturizer base include coconut alkanes, coco-caprylate/caprate, bio-chelated silica (i.e., bio-silicate fermentation product), and polysaccharide conditioner. As a lipophilic emollient, the texture enhancer helps improve skin feel of the gel texturizer base, essentially reducing the sticky feeling that would occur if the gel texturizer base contained only the solvent and the gum texture modifier. In other words, the texture enhancer reduces any sticky, gooey texture of the gel texturizer base, providing a skin feel finish. Thus, the texture enhancer of the gel texturizer base of the invention gives cosmetic products the ability to glide upon the skin surface, making the composition smooth and silky to apply.

The coconut alkanes of the texture enhancer is a non-polar oil, which is a mixture of C12 and C14. Coconut alkanes can be produced from the complete reduction and hydrogenation of a mixture of fatty acids derived from *Cocos nucifera* oil. The coconut alkanes of the instant invention are used in combination with coco-caprylate/caprate and, together, impart smoothing and emollient properties to the texture enhancer. In some embodiments, the coconut alkanes is a mixture about 25.0% to about 75.0% by weight of C12 alkalies and about 25.0% to about 75.0% by weight of C14 alkalies. In some embodiments, the coconut alkanes is a mixture of about 75.0% to about 95.0% by weight of C12 alkanes and about 5.0% to about 25.0% by weight of C14 alkanes. In some embodiments of the present invention, the coconut alkanes is a mixture of about 75.0% to about 90.0% by weight of C12 alkanes and about 10.0% to about 25.0% by weight of C14 alkanes. In some embodiments of the present invention, the coconut alkanes of the texture enhancer is about 85.0 to about 90.0% C12 alkanes. Coconut alkanes suitable for use in the texture enhancer are commercially available and can be purchased from, for example, Grant Industries, Inc. (Elmwood Park, NJ), Kobo Products, Inc. (South Plainfield, NJ), and Blue Sun International (Miami, FL).

In some embodiments, the texture enhancer contains about 70.0 to 98.0% coconut alkanes. In some embodiments, the texture enhancer contains about 75.0% coconut alkanes, or about 77.0%, about 78.0%, about 79.0%, about 80.0%, about 80.5%, about 81.0%, about 81.5%, about 82.0%, about 82.5%, about 83.0%, about 83.5%, about 84.0%, about 84.5%, about 85.0%, about 85.5%, about 86.0%, about 86.5%, about 87.0%, about 87.5%, about 88.0%, about 88.5%, about 89.0%, about 89.5%, about 90.0%, about 90.5%, about 91.0%, about 92.0%, about 93.0%, about 94.0%, or about 95.0% coconut alkanes. In some embodiments, the texture enhancer contains about 72.0 to 96.0% coconut alkanes, or about 73.4 to 96.5%, about 75.0 to 97.0%, about 75.0 to 96.0%, about 76.8 to 95.5%, about 78.2 to 94.0%, about 79.0 to 97.0%, about 80.0 to 95.0%, about 82.3 to 90.0%, about 83.5 to 91.0%, about 85.0 to 92.5%, about 86.8 to 93.8%, about 87.5 to 96.0%, about 88.0 to 95.0%, about 88.5 to 94.5%, about 88.0 to 94.0%, about 88.5 to 93.5%, about 89.0 to 92.5%, about 89.2 to 91.5%, about 89.5 to 90.0%, about 90.0 to 92.0%, about 90.0 to 95.0%, or about 90.0 to 98.0% coconut alkanes. In some embodiments, the texture enhancer contains about 87.0 to 92.0% coconut alkanes. In some embodiments, the texture enhancer contains about 88.0 to 91.0% coconut alkanes. In some embodiments, the texture enhancer contains about 89.0 to 90.5% coconut alkanes.

Coco-caprylate/caprate of the texture enhancer is a polar oil that is derived from a mixture of coconut fatty alcohol oil, caprylic acid, and capric acid. As mentioned above, the coco-caprylate/caprate is used together with the coconut alkanes to act as an emollient agent in the texture enhancer. It is a medium spreading emollient that is clear, mildly yellowish, medium polar oil, and a spreading value of approximately 800 mm$^2$/10 min. The coco-caprylate/caprate has a cloud point of 8-15° C., a viscosity of 9-12 cP, and a refraction (20° C.) of 1.4430-1.4470. The ester is prepared from the dehydration of C12-C18 coconut fatty alcohols with C8 caprylic acid and C10 capric acid. The esterification reaction will involve a catalyst, such as sulfuric acid, to form coco-caprylate/caprate from the coconut fatty alcohol and caprylic and capric acids. Because esterification is a reversible reaction, water must be removed to obtain a high-ester yield. One of skill in the art will appreciate the detailed steps and methods of ester synthesis, such as those included in *Bailey's Industrial Oil and Fat Products,* Sixth Edition, Six Volume Set, 2005, John Wiley & Sons, Inc., pages 1-56. Coco-caprylate/caprate suitable for use in the texture enhancer is commercially available and can be purchased from, for example, ABITEC Corporation (Columbus, OH), Grant Industries, Inc. (Elmwood Park, NJ), BASF Care Solutions LLC (Florham Park, NJ), SEPPIC (Fairfield, NJ), and Stéarinerie Dubois (Boulogne-Billancourt, France).

In some embodiments, the texture enhancer contains about 1.0 to 12.0% coco-caprylate/caprate. In some embodiments, the texture enhancer contains about 2.5% coco-caprylate/caprate, or about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, or about 10.0% coco-caprylate/caprate. In some embodiments, the texture enhancer contains about 1.5 to 11.0% coco-caprylate/caprate, or about 1.8 to 10.5%, about 2.0 to 10.0%, about 2.6 to 9.8%, about 3.3 to 9.4%, about 3.8 to 9.0%, about 4.0 to 8.5%, about 4.3 to 8.3%, about 4.6 to 7.8%, about 4.8 to 7.3%, about 5.0 to 6.8%, about 5.2 to 6.6%, about 5.4 to 6.2%, or about 5.6 to 6.0% coco-caprylate/caprate. In some embodiments, the texture enhancer contains about 4.0 to 6.5% coco-caprylate/caprate. In some embodiments, the texture enhancer contains about 4.5 to 6.0% coco-caprylate/caprate. In some embodiments, the texture enhancer contains about 5.0 to 6.0% coco-caprylate/caprate.

Bio-chelated silica, sometimes referred to as a bio-silicate fermentation product, is a bio-complexed silica extracted from fermented plant constituents (such as, for example, roots, leaves, stems, seeds, etc.). Bio-chelated silica is a natural alternative to inert, synthetic silicone elastomer fluids that are typically used in cosmetic compositions to provide a smooth, velvety and non-greasy or oily feel when applied to the skin. The bio-chelated silica of the instant invention is used in combination with polysaccharide conditioner and, together, provide epidermal slip, skin-feel properties, and sensory aesthetics to texture enhancer.

Any suitable plant constituent is useful for fermenting and producing the bio-silicate fermentation product for the texture enhancer. For example, plant constituents that can be processed to a fermentation broth include seeds, nodules, roots, leaves, stalks, stems, isolates, hydrolysates, or combinations thereof, which are obtained from suitable plants such as, for example, potatoes, rice, soya, *Triticum vulgare* L. (i.e., common wheat), barley, oats, rye, buckwheat, sugar cane, beans, *Arundinaria gigantea* (i.e., bamboo, giant cane, river cane, etc.), peas, linseeds, *Dipteryx odorata* (i.e., cumaru, tonka, etc.), cotton, sesame, *Agropyron cristatum* L. (i.e., crested wheat grass), okra, kola nut, lupins, rape, *Raphanus sativus* (i.e., radish), hemp, coconut palm, *Panicum miliaceum* L. (i.e., proso millet), sunflowers, peanuts, alfalfa, lucerne, *Nasturtium officinale* (i.e., watercress), hibiscus, tamarind, kwaokrua, broccoli, cauliflower, *Cytisus scoparius* (i.e., common broom plant), maca, quinoa, cocoa tree, mustards, almond, moringa, silk, kale, baobab, cassia, irvingia, wallflower, thistle, oil palm, or combinations thereof. In some embodiments, the bio-chelated silica is derived from the constituents obtained from sugar cane, rice, soya, *Triticum vulgare* L. (i.e., common wheat), oats, rye, beans, *Panicum miliaceum* L. (i.e., proso millet), *Arundinaria gigantea* (i.e., bamboo, giant cane, river cane, etc.), peas, *Dipteryx odorata* (i.e., cumaru, tonka, etc.), cotton, okra, kola nut, lupins, rape, *Raphanus sativus* (i.e., radish), *Agropyron cristatum* L. (i.e., crested wheat grass), sunflowers, peanuts, alfalfa, lucerne, *Nasturtium officinale* (i.e., watercress), tamarind, broccoli, cauliflower, *Cytisus scoparius* (i.e., common broom plant), kwaokrua, cocoa tree, baobab, thistle, mustards, kale, wallflower, or combinations thereof. In some embodiments, the bio-chelated silica is derived from the constituents obtained from rice, soya, *Triticum vulgare* L. (i.e., common wheat), oats, rye, sugar cane, beans, *Arundinaria gigantea* (i.e., bamboo, giant cane, river cane, etc.), peas, *Dipteryx odorata* (i.e., cumaru, tonka, etc.), *Agropyron cristatum* L. (i.e., crested wheat grass), lupins, rape, *Raphanus sativus* (i.e., radish), *Panicum miliaceum* L. (i.e., proso millet), peanuts, alfalfa, *Nasturtium officinale* (i.e., watercress), tamarind, broccoli, cauliflower, *Cytisus scoparius* (i.e., common broom plant), mustards, kale, wallflower, or combinations thereof.

In some embodiments, the bio-chelated silica is derived from the constituents obtained from plants of the Asteraceae family, Lamiaceae family, Poaceae family, Fabaceae family, Brassicaceae family, Rosaceae family, Malvaceae family, or combinations thereof. In some embodiments, the bio-chelated silica is derived from the constituents obtained from plants of the Poaceae family, Fabaceae family, Brassicaceae family, or combinations thereof. In some embodiments, the bio-chelated silica is derived from the constituents obtained from plants of the Poaceae family, Fabaceae family, and Brassicaceae family. In some embodiments, the bio-chelated silica is derived from the constituents obtained from Fabaceae family and the Brassicaceae family. In some embodiments, the bio-chelated silica is derived from the constituents obtained from Poaceae family and Fabaceae family. In some embodiments, the bio-chelated silica is derived from the constituents obtained from Poaceae family and Brassicaceae family. In some embodiments, the bio-chelated silica is derived from the constituents obtained from plants of the Poaceae family, Fabaceae family, and Brassicaceae family.

In some embodiments, the bio-chelated silica is derived from the constituents obtained from plants of the Poaceae family. In some embodiments, the bio-chelated silica is derived from the constituents obtained from sugar cane, rice, *Triticum vulgare* L. (i.e., common wheat), oats, rye, *Panicum miliaceum* L. (i.e., proso millet), *Arundinaria gigantea* (i.e., bamboo, giant cane, river cane, etc.), *Agropyron cristatum* L. (i.e., crested wheat grass), or combinations thereof. In some embodiments, the bio-chelated silica is derived from the constituents obtained from plants of the Fabaceae family. In some embodiments, the bio-chelated silica is derived from the constituents obtained from soya, beans, peas, *Dipteryx odorata* (i.e., cumaru, tonka, etc.), lupins, peanuts, alfalfa, tamarind, *Cytisus scoparius* (i.e., common broom plant), or combinations thereof. In some embodiments, the bio-chelated silica is derived from the constituents obtained from plants of the Brassicaceae family. In some embodiments, the bio-chelated silica is derived from the constituents obtained from rape, *Raphanus sativus* (i.e., radish), *Nasturtium officinale* (i.e., watercress), broccoli, cauliflower, mustards, kale, wallflower, or combinations thereof.

In some embodiments, the bio-chelated silica is derived from the constituents obtained from *Arundinaria gigantea* (i.e., bamboo, giant cane, river cane, etc.), *Dipteryx odorata* (i.e., cumaru, tonka, etc.), cotton, okra, kola nut, *Raphanus sativus* (i.e., radish), or combinations thereof. In some embodiments, the bio-chelated silica is derived from the constituents obtained from *Arundinaria gigantea* (i.e., bamboo, giant cane, river cane, etc.), *Dipteryx odorata* (i.e., cumaru, tonka, etc.), *Raphanus sativus* (i.e., radish), or combinations thereof. In some embodiments, the bio-chelated silica is derived from the constituents obtained from *Dipteryx odorata* (i.e., cumaru, tonka, etc.) and *Raphanus sativus* (i.e., radish). In some embodiments, the bio-chelated silica is derived from the constituents obtained from *Arundinaria gigantea* (i.e., bamboo, giant cane, river cane, etc.) and *Dipteryx odorata* (i.e., cumaru, tonka, etc.). In some embodiments, the bio-chelated silica is derived from the constituents obtained from *Arundinaria gigantea* (i.e., bamboo, giant cane, river cane, etc.) and *Raphanus sativus* (i.e., radish). In some embodiments, the bio-chelated silica is derived from the constituents obtained from the combination of *Arundinaria gigantea* (i.e., bamboo, giant cane, river cane, etc.), *Dipteryx odorata* (i.e., cumaru, tonka, etc.), and *Raphanus sativus* (i.e., radish). In some embodiments, the bio-chelated silica is derived from the constituents obtained from *Raphanus sativus* (i.e., radish). In some embodiments, the bio-chelated silica is derived from the constituents obtained from *Dipteryx odorata* (i.e., cumaru, tonka, etc.). In some embodiments, the bio-chelated silica is derived from the constituents obtained from *Arundinaria gigantea* (i.e., bamboo, giant cane, river cane, etc.).

The bio-chelated silica (i.e., the bio-silicate fermentation product) can be obtained using suitable fermenting methods known in the art. The fermentation technique should result in a bio-silicate fermentation product that preserves the bioactive components of the plant. An exemplary method of obtaining the bio-chelated silica involves harvesting the suitable plant biomass (i.e., size-reduced plant parts, plant extracts, size-reduced and/or extracted seeds, nodules, roots, stems, stalks or leaves, hydrolysates or isolates, protein concentrates, etc.), preparing the harvested biomass for the extraction process, preparing the fermentation broth/extraction, inoculation and fermentation with suitable lactic acid bacteria (e.g., *Lactobacillus* spp., spp., etc.), and, optionally, at least one yeast. The bio-silicate fermentation product is isolated from the fermentation broth and isolated as a solid precipitate or as a solution to for use in the texture enhancer. Detailed methods of preparing a bio-silicate fermentation product are described in U.S. Patent Application Publication US 2005/0089499, which is incorporated herein by reference.

The plant biomass used for obtaining the bio-silicate fermentation product is harvested and prepared for extraction using methods described previously for plant juice solvent. The plant biomass used for fermentation is prepared using suitable conventional extraction processes, such as maceration, re-maceration, digestion, agitation maceration, vortex extraction, ultrasonic extraction, countercurrent extraction, percolation, re-percolation, evacolation (extraction under reduced pressure), diacolation and solid/liquid extraction under continuous reflux in a Soxhlet extractor, which are familiar to the expert and which may all be used in principle, can be found, for example, in Hagers Handbuch der pharmazeutischen Praxis (5th Edition, Vol. 2, pp. 1026-1030, Springer Verlag, Berlin-Heidelberg-New York 1991). In some embodiments, the plant biomass used for fermentation is prepared from the maceration of the stalks and leaves of *Arundinaria gigantea* (i.e., bamboo). In some embodiments, the plant biomass used for fermentation is prepared from the maceration of the seeds (i.e., beans) of *Dipteryx odorata* (i.e., tonka bean). In some embodiments, the plant biomass used for fermentation is prepared from the maceration of the roots of *Raphanus sativus* (i.e., radish).

The fermentation broth can be prepared by extraction of the plant material with water in the mildly alkaline range and removal of any insoluble solids via filtration or centrifuging, which may be optionally repeated. Alternatively, the extraction process may be carried out in an aqueous medium, in the acidic range, the proteins being precipitated, separated off and re-dissolved in water in the mildly alkaline range. In some embodiments, the bamboo stalks and leaves are size-reduced, ground and dispersed in water or alkaline aqueous medium, and directly fermented without further extraction or working up.

To prepare the fermentation broth, other typical additives may be incorporated in these starting materials including, for example, soya peptone, malt extract or fermentable sugars (for example sucrose or glucose). The fermentation broth can be adjusted to a starting pH of about 4.5 to a pH of about 8.5, followed by the inoculation step using lactic acid bacteria and, optionally, yeasts. The lactic acid bacteria and optional yeast may be used in different quantities and ratios by weight. For example, the bacteria *Lactobacillus lactis* can be used in quantities of $10^2$ to $10^8$ CFU/mL. The ratio by weight of the various lactic acid bacteria to one another, i.e. *Lactobacillus, Lactococcus* and *Leuconcostoc,* may be from 1:1000 to 1000:1 and is preferably from 1:100 to 100:1. The yeasts may be used in quantities of $10^2$ to $10^7$ CFU/mL. The ratio by weight between bacteria and enzymes may ultimately be 1:100000 to 100000:1 or 1:1000 to 1000:1.

Fermentation can be carried out at temperatures of 20 to 37° C. in a static or closed stirred tank for 12 and 48 hours. In some embodiments, the fermentation of bamboo stalks and leaves is performed using the bacteria *Lactobacillus lactis*. In some embodiments, the fermentation of tonka beans is performed using the bacteria *Lactobacillus lactis*. In some embodiments, the fermentation of radish roots is performed using the bacteria *Leuconcostoc lactis*. In the course of the fermentation process, the fermentable sugars are converted into organic acids, ethanol, carbon dioxide and aromatics, with a fall in the pH to about 4 or 5. In addition, a bio-silicate is formed with the silica from the plant matrix. The resulting fermentation product can be recovered using separation techniques known per se such as, for example, centrifuging, membrane filtration (microfiltration, ultrafiltration, nanofiltration), liquid/liquid or solid phase extraction, chromatography, precipitation from solvents and the like. The microorganisms still present in the fermentation products are removed using known techniques, such as heat treatment (pasteurization, sterilization), cell destruction, microfiltration, centrifuging and the like.

The bio-silicate fermentation product may be a solid precipitate, or isolated as a solution by lowering the pH. In some embodiments, the bio-silicate fermentation product is *Lactobacillus/Arundinaria gigantea* leaf ferment filtrate, *Lactobacillus/Dipteryx odorata* seed ferment filtrate, *Leuconcostoc/Raphanus sativus* (radish) root ferment filtrate, or combinations thereof. In some embodiments, the bio-silicate fermentation product is the combination of *Lactobacillus/Dipteryx odorata* seed ferment filtrate and *Leuconcostoc/Raphanus sativus* root ferment filtrate. In some embodiments, the bio-silicate fermentation product is the combination of *Lactobacillus/Arundinaria gigantea* leaf ferment filtrate and *Lactobacillus/Dipteryx odorata* seed ferment filtrate. In some embodiments, the bio-silicate fermentation product is the combination of *Lactobacillus/Arundinaria gigantea* leaf ferment filtrate and *Leuconcostoc/Raphanus sativus* root ferment filtrate. In some embodiments, the bio-silicate fermentation product is the combination of *Lactobacillus/Arundinaria gigantea* leaf ferment filtrate, *Lactobacillus/Dipteryx odorata* seed ferment filtrate, and *Leuconcostoc/Raphanus sativus* root ferment filtrate. In some embodiments, the bio-silicate fermentation product is *Leuconcostoc/Raphanus sativus* root ferment filtrate. In some embodiments, the bio-silicate fermentation product is *Lactobacillus/Dipteryx odorata* seed ferment filtrate. In some embodiments, the bio-silicate fermentation product is *Lactobacillus/Arundinaria gigantea* leaf ferment filtrate.

In some embodiments, the bio-silicate fermentation product is a viscous liquid having an acidic to neutral pH of between about 3.5 and about 7.0. In some embodiments, the bio-silicate fermentation product is *Leuconcostoc/Raphanus sativus* root ferment filtrate having an acidic pH of between about 4.0 and about 6.0. In some embodiments, the bio-silicate fermentation product is *Lactobacillus/Dipteryx odorata* seed ferment filtrate having an acidic to neutral pH of between about 5.0 and about 7.0. In some embodiments, the bio-silicate fermentation product is *Lactobacillus/Arundinaria gigantea* leaf ferment filtrate having an acidic pH of between about 3.5 and about 6.0. In some embodiments, the bio-silicate fermentation product is a combination of *Lactobacillus/Dipteryx odorata* seed ferment filtrate and *Leuconcostoc/Raphanus sativus* root ferment filtrate, having an acidic pH of between about 4.0 and about 6.5. In some embodiments, the bio-silicate fermentation product is the combination of *Lactobacillus/Arundinaria gigantea* leaf ferment filtrate and *Lactobacillus/Dipteryx odorata* seed ferment filtrate, having an acidic pH of between about 3.5 and about 6.5. In some embodiments, the bio-silicate fermentation product is the combination of *Lactobacillus/Arundinaria gigantea* leaf ferment filtrate and *Leuconcostoc/Raphanus sativus* root ferment filtrate, having an acidic pH of between about 3.5 and about 6.5. In some embodiments, the bio-silicate fermentation product is the combination of *Lactobacillus/Arundinaria gigantea* leaf ferment filtrate, *Lactobacillus/Dipteryx odorata* seed ferment filtrate, and *Leuconcostoc/Raphanus sativus* root ferment filtrate, having an acidic pH of between about 3.5 and about 6.8.

In some embodiments, the bio-silicate fermentation product has an acidic to neutral pH of between about 3.5 and about 7.0, a bacterial cell count of less than 100 CFU/g, and a yeast and mold content of less than 100 CFU/g. For example, the bio-silicate fermentation product can be *Lactobacillus/Arundinaria gigantea* leaf ferment filtrate having an acidic pH of between about 3.5 and about 6.0, a bacterial cell count of less than 100 CFU/g, and a yeast and mold content of less than 100 CFU/g. The bio-silicate fermentation product suitable for use in the texture enhancer is commercially available and can be purchased from, for example, The Garden of Naturalsolution Co., Ltd. (Gyeonggi-do, South Korea), Active Micro Technologies, LLC (Lincolnton, North Carolina), Greentech USA (Yarmouth, ME), Sederma SAS (Yvelines, France), and Active Concepts, LLC (Lincolnton, NC).

In some embodiments, the texture enhancer contains about 0.50 to 10.0% bio-silicate fermentation product. In some embodiments, the texture enhancer contains about 1.0% bio-silicate fermentation product, or about 1.3%, about 1.5%, about 1.8%, about 2.0%, about 2.5%, about 2.8%, about 3.0%, about 3.5%, about 4.0%, about 4.5%, about 5.0%, about 5.5%, about 6.0%, about 6.5%, about 7.0%, about 7.5%, or about 8.0% bio-silicate fermentation product. In some embodiments, the texture enhancer contains about 0.75 to 9.0% bio-silicate fermentation product, or about 0.80 to 8.4%, about 1.0 to 7.2%, about 1.2 to 6.3%, about 1.4 to 5.0%, about 1.5 to 4.3%, about 1.8 to 3.8%, about 2.0 to 3.2%, about 2.1 to 2.8%, or about 2.3 to 2.5% bio-silicate fermentation product. In some embodiments, the texture enhancer contains about 1.5 to 3.5% bio-silicate fermentation product. In some embodiments, the texture enhancer contains about 2.0 to 3.5% bio-silicate fermentation product. In some embodiments, the texture enhancer contains about 2.0 to 3.0% bio-silicate fermentation product.

The polysaccharide conditioner of the texture enhancer is a high molecular weight, water soluble carbohydrate polymer produced by a microorganism. Similar to the bio-chelated silica, the polysaccharide conditioner is a natural alternative to inert, synthetic silicone elastomer fluids. The polysaccharide conditioner, when combined with the other ingredients of the texture enhancer, acts as a sensorial modifier contributing to the overall non-greasy feel of the gel texturizer base. In fact, the specific combination of the polysaccharide conditioner and bio-silicate fermentation product imparts skin conditioning properties to the texture enhancer, thereby improving the sensory perception of the gel texturizer base.

The polysaccharide conditioner of the texture enhancer is any suitable hetero-polysaccharide having repeating units of any two or more saccharides, such as, for example, fucose residues, glucose residues, fructose residues, rhamnose residues, glucuronic acid residues, mannose residues, galactose residues, galacturonic acid residues, and derivatives thereof. In some embodiments, the polysaccharide conditioner is a hetero-polysaccharide having a repetition of any three of the following saccharides: fucose residues, galacturonic acid residues, rhamnose residues, galactose residues, glucuronic acid residues, glucose residues, fructose residues, and derivatives thereof. In some embodiments, the polysaccharide conditioner is a hetero-polysaccharide with repeating units of fucose, galactose, and galacturonic acid residues. In some embodiments, the polysaccharide conditioner is a hetero-polysaccharide with repeating units of rhamnose, galactose, and glucuronic acid residues. In some embodiments, the polysaccharide conditioner is a hetero-polysaccharide with repeating units of fucose, glucose, and glucuronic acid residues.

In some embodiments, the polysaccharide conditioner is a hetero-polysaccharide obtained by the bacterial fermentation of non-genetically modified soy and/or corn (i.e., sorbitol). In some embodiments, the polysaccharide conditioner is a biosaccharide gum, such as, for example, biosaccharide gum-1, biosaccharide gum-2, biosaccharide gum-3, biosaccharide gum-4, and biosaccharide gum-5. In some embodiments, the polysaccharide conditioner is biosaccharide gum-1. Polysaccharide conditioners suitable for use in the texture enhancer are commercially available and can be purchased from, for example, Solabia Group (Pantin, France) and SMA Collaboratives, LLC (Pompano Beach, FL).

In some embodiments, the texture enhancer contains about 0.50 to 10.0% polysaccharide conditioner. In some embodiments, the texture enhancer contains about 1.0% polysaccharide conditioner, or about 1.3%, about 1.5%, about 1.8%, about 2.0%, about 2.5%, about 2.8%, about 3.0%, about 3.5%, about 4.0%, about 4.5%, about 5.0%, about 5.5%, about 6.0%, about 6.5%, about 7.0%, about 7.5%, or about 8.0% polysaccharide conditioner. In some embodiments, the texture enhancer contains about 0.75 to 9.0% polysaccharide conditioner, or about 0.80 to 8.4%, about 1.0 to 7.2%, about 1.2 to 6.3%, about 1.4 to 5.0%, about 1.5 to 4.3%, about 1.8 to 3.8%, about 2.0 to 3.2%, about 2.1 to 2.8%, or about 2.3 to 2.5% polysaccharide conditioner. In some embodiments, the texture enhancer contains about 1.5 to 3.5% polysaccharide conditioner. In some embodiments, the texture enhancer contains about 2.0 to 3.5% polysaccharide conditioner. In some embodiments, the texture enhancer contains about 2.0 to 3.0% polysaccharide conditioner.

As mentioned previously, the combination of the bio-chelated silica and polysaccharide conditioner within the texture enhancer imparts additional film-forming properties and a silky, smooth feeling to the gel texturizer base of the instant invention. As such, the weight to weight ratio of the bio-silicate fermentation product to the polysaccharide conditioner of the texture enhancer of the gel texturizer base of the invention will range from 0.45 to 1.5. For example, a texture enhancer containing 88.0% coconut alkanes and 6.0% coco-caprylate/caprate, can also have 3.1% of the bio-silicate fermentation product, and 2.9% of the polysaccharide conditioner. Thus, the weight to weight ratio of the bio-silicate fermentation product to the polysaccharide conditioner of the texture enhancer is 1.07 (i.e., 3.1:2.9=1.07). In some embodiments, the weight to weight ratio of the bio-silicate fermentation product to the polysaccharide conditioner of the texture enhancer can be about 0.60, 0.65, 0.70, 0.75, 0.80, 0.85, 0.90, 0.95, 1.0, or about 1.3. In some embodiments, the weight to weight ratio of the bio-silicate fermentation product to the polysaccharide conditioner of the texture enhancer ranges from 0.5 to 1.5, or from 0.6 to 1.4, or 0.75 to 1.3, or from 0.8 to 1.2, or from 0.85 to 1.15. In some embodiments, the weight to weight ratio of the bio-silicate fermentation product to the polysaccharide conditioner of the texture enhancer ranges from 0.9 to 1.1. In some embodiments, the weight to weight ratio of the bio-silicate fermentation product to the polysaccharide conditioner of the texture enhancer is 1.0.

In some embodiments, the texture enhancer of the gel texturizer base comprises coconut alkanes in the amount of about 70.0 to 98.0%, coco-caprylate/caprate in the amount of about 1.0 to 12.0%, the bio-silicate fermentation product in the amount of about 0.50 to 10.0%, and the polysaccharide conditioner in the amount of about 0.50 to 10.0%. In some embodiments, the texture enhancer of the gel texturizer base comprises coconut alkanes in the amount of about 80.0 to 95.0%, coco-caprylate/caprate in the amount of about 3.3 to 9.4%, the bio-silicate fermentation product in the amount of about 1.4 to 5.0%, and the polysaccharide conditioner in the amount of about 1.4 to 5.0%. In some embodiments, the texture enhancer of the gel texturizer base comprises coconut alkanes in the amount of about 87.0 to 92.0%, coco-caprylate/caprate in the amount of about 4.0 to 6.5%, the bio-silicate fermentation product in the amount of about 1.5 to 3.5%, and the polysaccharide conditioner in the amount of about 1.5 to 3.5%. In some embodiments, the texture enhancer of the gel texturizer base comprises coconut alkanes in the amount of about 88.0 to 91.0%, coco-caprylate/caprate in the amount of about 4.5 to 6.0%, the bio-silicate fermentation product in the amount of about 2.0 to 3.5%, and the polysaccharide conditioner in the amount of about 2.0 to 3.5%. In some embodiments, the texture enhancer of the gel texturizer base comprises coconut alkanes in the amount of about 89.0 to 90.5%, coco-caprylate/caprate in the amount of about 5.0 to 6.0%, the bio-silicate fermentation product in the amount of about 2.0 to 3.0%, and the polysaccharide conditioner in the amount of about 2.0 to 3.0%.

Gum Texture Modifiers

The gum texture modifier component of the gel texturizer base of the invention is a combination of gelling agents and thickeners, sometimes referred to as the "gelator" of the dispersion system. The gum texture modifier is a flowable powder that is off-white in color. The constituents of the gum texture modifier of the gel texturizer base include clay, polysaccharide thickener, polysaccharide stabilizer, and glyceryl stearate or glyceryl stearate SE. The gum texture modifier not only thickens the fluid of the gel matrix and suspends dispersions of additives in the fluid (i.e., the solvent), it also improves the stability of such ensuing dispersion formulations, the details of which are described in the present application.

The clay of the gum texture modifier is an interactive filler and swelling agent which is used to impart significant viscosity and thixotropic enhancement to the base fluid (i.e., the solvent) without significant elasticity. The clay of the gum texture modifier is water-washed, natural, has a net negative charge, and is capable of swelling when dispersed throughout the hydrophilic phase (i.e., the solvent) and lipophilic phase (i.e., the texture enhancer) of the gel texturizer base. The swelling properties of these natural clay minerals permit colloidal particles to form upon hydration, which are able to maintain a uniform suspension in solution and allowing the formation of a gel with rheological characteristics that are typical of the clay mineral used.

Clays are products that are already well known per se, which are described, for example, in the publication "Minéralogie des argiles [Mineralogy of Clays]," S. Caillère, S. Hénin, M. Rautureau, 2nd Edition 1982, Masson, the teaching of which is included herein by reference. Clays are silicates containing a cation that may be chosen from calcium, magnesium, aluminum, sodium, potassium and lithium cations, and mixtures thereof. In some embodiments, the clay of the gum texture modifier is a clay of the smectite family, vermiculite family, stevensite family, or chlorite family. In some embodiments, the clay of the gum texture modifier is a smectite clay.

Smectite clays have characteristic layered structures and consequently individual crystals have a flake or platelet shape. Smectites are composed of two silica tetrahedral sheets with a central octahedral sheet and are designated as a 2:1 phyllosilicates. Water molecules and cations occupy the space between the 2:1 layers (See, Bergava, F., et al. 2006, *Handbook of Clay Science*, Elsevier Scientific Publisher (1st ed.), p. 15). In a unit layer of smectite, the continuous central octahedral layer can contain alumina or magnesia, which is bound between two tetrahedral silica sheets through three bridging oxygens, thereby forming linked rings with hexagonal openings. A single smectite clay crystal layer is about 1 nanometer thick, while the lateral dimensions of these layers vary from 200 nm to several microns depending on the particular clay mineral. See, Patel, H., et al. 2010 *Household and Personal Care today* (4) 31-36.

The isomorphic substitution in octahedral or tetrahedral generates net negative charges at the surface of the weakly bound platelets, which allows water and other polar molecules to enter within the interlayer space of the stacked layers. Isomorphic substitution within the layer (either in octahedral or tetrahedral site) by $Mg^{2+}$, $Fe^{2+}$ or $Al^{3+}$ generates negative charges that can be counter balanced by hydrated alkali or alkaline earth cations ($Na^+$, $K^+$, $Ca^{2+}$, $Li^+$, etc.). For example, when the predominant octahedral cation is $Al^{3+}$, as in montmorillonite, the clay lattice is charge balanced by filling two of every three octahedral positions (i.e., dioctahedral clay). If the predominant octahedral cation is $Mg^{2+}$, as in saponite and hectorite, all three of the octahedral positions are filled (i.e., trioctahedral clay) See, Patel, H., et al. 2010 *Household and Personal Care today* (4) 31-36.

In some embodiments, the smectite clay of the gum texture modifier is a trilayer clay, such as, for example, montmorillonites, hectorites, bentonites, attapulgites, sepiolites, beidellites, saponites, or mixtures thereof. In some embodiments, the smectite clay of the gum texture modifier is montmorillonite, bentonite, hectorite, or mixtures thereof. In some embodiments, the smectite clay of the gum texture modifier is bentonite. Bentonite is an ore or product with substantial smectite content, most often montmorillonite. In some embodiments, the clay used in the gum texture modifier is natural and water-washed bentonite clay. Clays suitable for use in the gum texture modifier are commercially available and can be purchased from, for example, Vanderbilt Minerals, LLC (Norwalk, CT), Spectrum Chemical Mfg. Corp. (New Brunswick, NJ), The Innovation Company (Dreux, France), and Eckart America Corporation (Painesville, OH).

In some embodiments, the gum texture modifier contains about 30.0 to 70.0% of the clay. In some embodiments, the gum texture modifier contains about 33.0% of the clay, or about 35.0%, about 37.5%, about 39.2%, about 41.2%, about 43.0%, about 44.8%, about 46.2%, about 47.8%, about 49.2%, about 52.5%, about 53.5%, about 54.5%, about 56.0%, about 56.5%, about 57.0%, about 59.0%, or about 64.0% of the clay. In some embodiments, the gum texture modifier contains about 38.0 to 62.0% of the clay, or about 41.0 to 60.8%, about 42.5 to 59.5%, about 43.0 to 58.0%, about 44.0 to 57.2%, about 45.8 to 55.5%, about 46.5 to 54.0%, about 47.0 to 52.0%, about 48.0 to 51.5%, about 48.2 to 50.8%, or about 48.5 to 49.5% of the clay. In some embodiments, the gum texture modifier contains about 44.5 to 53.0% of the clay. In some embodiments, the gum texture modifier contains about 46.0 to 51.0% of the clay. In some embodiments, the gum texture modifier contains about 47.5 to 50.0% of the clay.

The polysaccharide thickener of the gum texture modifier is a rheological control agent which is used to impart viscosity as well as elasticity to the base fluid of the dispersion network. The polysaccharide thickener of the gum texture modifier is a natural polymer, which, when combined with a polysaccharide stabilizer and glyceryl stearate or glyceryl stearate SE, helps build the viscoelastic network in the dispersion matrix. Also a suspending agent, the polysaccharide thickener of the gum texture modifier helps prevent sedimentation of solid particulates (i.e., the clay) of the gel texturizer base.

Polysaccharide thickeners are a type of naturally derived polymers constructed with simple sugar building blocks that become hydrated in an aqueous environment. In some embodiments, the polysaccharide thickeners are anionic polysaccharides, cationic polysaccharides, nonionic polysaccharides, or amphoteric polysaccharides. In some embodiments, the polysaccharide thickener of the gum texture modifier is a microbial polysaccharide. Polysaccharide thickeners useful in the gum texture modifier include, but are not limited to, pectin, gum arabic, acacia gum, tragacanth gum, ghatti gum, cassia gum, tara gum, carob gum, karaya gum, xanthan gum, chitosan, and guar gum. In some embodiments, the polysaccharide thickener of the gum texture modifier can be pectin, gum arabic, tragacanth gum, karaya gum, xanthan gum, chitosan, guar gum, or combinations thereof. In some embodiments, the polysaccharide thickener can be xanthan gum.

Xanthan gum is a high molecular weight heteropolysaccharide gum produced by a pure-culture fermentation of a carbohydrate with *Xanthomonas campestris*. Xanthan gum is composed of glucose, glucuronic acid, 6-acetylmannose, and 4,6-pyruvylated mannose residues. The double helical structure of xanthan gum undergoes significant hydrogen bonding in solution, forming a weak three-dimensional network structure when at rest or when subjected to very low deformations. Under high deformations, the three dimensional structure is easily broken down, imparting rheological behavior. Polysaccharide thickeners suitable for use in the gum texture modifier are commercially available and can be purchased from, for example, Vanderbilt Minerals, LLC (Norwalk, CT), Spectrum Chemical Mfg. Corp. (New Brunswick, NJ), BASF Care Solutions LLC (Florham Park, NJ), and Solvay Novecare S.A. (Brussels, Belgium).

In some embodiments, the gum texture modifier contains about 10.0 to 32.0% of the polysaccharide thickener. In some embodiments, the gum texture modifier contains about 13.5% of the polysaccharide thickener, or about 16.0%, about 17.5%, about 19.0%, about 21.0%, about 23.0%, about 25.0%, about 27.0%, about 29.0%, about 31.0%, or about 33.0% of the polysaccharide thickener. In some embodiments, the gum texture modifier contains about 12.0 to 36.4% of the polysaccharide thickener, or about 14.5 to 33.2%, about 16.2 to 31.5%, about 18.8 to 29.4%, about 19.0 to 28.0%, about 20.0 to 26.2%, about 21.0 to 25.0%, or about 21.8 to 23.8% of the polysaccharide thickener. In some embodiments, the gum texture modifier contains about 19.5 to 25.0% of the polysaccharide thickener. In some embodiments, the gum texture modifier contains about 20.0 to 24.0% of the polysaccharide thickener. In some embodiments, the gum texture modifier contains about 21.0 to 23.0% of the polysaccharide thickener.

The polysaccharide stabilizer of the gum texture modifier is thixotropic agent and natural structuring polymer that exhibits a strong three-dimensional structure in lean solvent systems while providing optimum rheological characteristics. The polysaccharide stabilizer works with the clay of the gum texture modifier to provide additional thixotropic properties to the gel texturizer base. These thixotropic properties allow the gel base to exhibit a stable form at rest, but become more fluid when agitated. The polysaccharide stabilizer strengthens the gel matrix structure with the polysaccharide thickener and glyceryl stearate or glyceryl stearate SE.

For the purpose of the present invention, polysaccharide stabilizers include naturally derived polymers prepared from seaweed or algae, such as, for example, brown seaweed or brown algae, red seaweed or red algae, green algae, or red-purple algae. In some embodiments, the polysaccharide stabilizer is alginate isolated from brown seaweed, agar isolated from red algae, fucoidan isolated from brown algae, agarose isolated from red algae, carrageenan isolated from red seaweed, ulvan isolated from green algae, or combinations thereof. In some embodiments, the polysaccharide stabilizer is a sulfated galactose-based polysaccharide prepared from seaweed or algae, such as, for example, agar, carrageenan, ulvan, alginate, fucoidan, or combinations thereof. In some embodiments, the polysaccharide stabilizer is a sulfated galactose-based polysaccharide prepared from seaweed selected from agar, carrageenan, or alginate. In some embodiments, the polysaccharide stabilizer of the gum texture modifier is a sulfated galactose-based polysaccharide prepared from red seaweed or algae. In some embodiments, the polysaccharide stabilizer is a sulfated galactose-based polysaccharide prepared from seaweed or algae can be carrageenan.

The polysaccharide stabilizer, such as carrageenan, can be obtained by systematically gathering seaweed, followed by quickly drying and baling the seaweed to maintain its quality. At the manufacturing site the dried seaweed is mechanically ground and sieved to eliminate impurities such as sand and salt. Following extensive washing to ensure additional quality, the seaweed undergoes a hot extraction process to separate the polysaccharide stabilizer (e.g., carrageenan) from the extraneous plant fiber. Removal of the cellulosic material requires a two-step clarification process. First, the dissolved polysaccharide stabilizer mixture (i.e., carrageenan) is centrifuged to eliminate dense cellulosic particles. Then, filtration is used to remove the smaller particles. The solution is then concentrated by evaporation to accommodate the removal of water. The concentrated polysaccharide stabilizer solution (i.e., carrageenan) is precipitated in a suitable solvent, such as, for example, isopropyl alcohol. For instance, because carrageenan is insoluble in alcohol, the carrageenan filtrate turns into a coagulum of carrageenan, alcohol and water. The coagulum is compressed to remove the liquids and vacuum dried to completely remove the alcohol. Drying is completed on a belt drier and the dried coagulum is then ground to specification. Polysaccharide stabilizers suitable for use in the gum texture modifier are commercially available and can be purchased from, for example, SEPPIC (Paris, France), FMC Health and Nutrition (Philadelphia, PA), and Caribbean Natural Products Inc. (Fairfield, NJ).

Carrageenan is a high molecular weight sulfated cell wall polysaccharide found in red seaweed and red algae, containing repeating sulfated and unsulfated disaccharides of galactose and 3,6-anhydrogalactose. The units are joined by alternating α-1-3 and β-1-4 glycosidic linkages. Carrageenans are classified into three main categories: kappa (κ); iota (ι); and lambda (λ). The three types of carrageenan molecules differ by (1) the types of linkages between the galactose units, and (2) the point of attachment of the sulfate groups to the galactose units. These apparently small differences in chemical constitution and structure make major differences in the gelling and structuring properties of each type of molecule.

Kappa carrageenans produce strong rigid gels, exhibit some syneresis (i.e., contraction accompanied by the expulsion of a liquid from a gel), and form helices with potassium ions. Introduction of calcium ions causes κ-carrageenans helices to aggregate. As a result, the gel contracts and becomes brittle. Kappa carrageenans are characterized by an ester sulfate content of approximately 25% (theoretically having 1 sulfate group per repeating unit; the most naturally abundant type of carrageenan molecule). Iota carrageenans, on the other hand, form more flaccid, compliant, and elastic gels. In addition, iota carrageenans also form helices with calcium ions. Aggregation is limited in ι-carrageenans, and ι-carrageenans do not undergo syneresis. Iota carrageenans are characterized by an ester sulfate content of approximately 32% (theoretically having 2 sulfate groups per repeating unit; the least naturally abundant type of carrageenan molecule). Lambda carrageenans theoretically have 3 sulfate groups per repeating unit, which causes the sugar molecules to assume the flat 4-C-1 confirmation. Because of this flat structure, λ-carrageenans do not gel in water, exhibit a random distribution of polymer chains, and interact strongly with proteins. Lambda carrageenans are characterized by an ester sulfate content of approximately 35%.

Some types of seaweed species contains relatively pure carrageenan fractions. *Kappaphycus alvarezii* contains largely κ carrageenan and μ carrageenan which may be converted to kappa carrageenan by alkali treatment. *Eucheuma denticulatum* contains a similarly high level of ι-carrageenan with some ν carrageenan precursor. Other seaweeds are more mixed in their carrageenan content. *Furcellaran* contains a strong gelling type carrageenan which is a mix of κ carrageenan and β carrageenan in a roughly 3:2 ratio. Other seaweed types, such as *Chondrus crispus* and *Gigartina* types contain not only a mix of κ and λ type carrageenans, but also a type of carrageenan polymer that is essentially a block copolymer of different carrageenan types. This gives the carrageenan made from *Gigartina* or *Chondrus* weed species quite different properties from those made from the *Eucheuma* type species from South east Asia.

In some embodiments, the polysaccharide stabilizer of the gum texture modifier is kappa-carrageenan, iota-carrageenan, lambda-carrageenan, or a carrageenan mixture thereof. The determination of the effective proportion of kappa-, iota-, and lambda-carrageenans in the polysaccharide stabilizer is dependent upon the desired balance of gel efficiency and consistency requirements, and the rheological characteristics associated therewith. For the purposes of the instant invention, carrageenan mixtures of kappa-carrageenan, iota-carrageenan, and lambda-carrageenan should include only a minimal amount of lambda-carrageenan. As such, the proportion of lambda-carrageenan in the carrageenan mixture should not be above about 20% by weight of the carrageenan mixture, preferably not above about 12% by weight. In some embodiments, the polysaccharide stabilizer of the gum texture modifier is a carrageenan mixture of kappa-carrageenan and iota-carrageen. In some embodiments, the carrageenan mixture of kappa-carrageenan and iota-carrageen may consist of, or consist essentially of, about 25% to about 75% by weight of kappa-carrageenans and about 25% to about 75% by weight of iota-carrageenans. In some embodiments, the carrageenan mixture of kappa-carrageenan and iota-carrageen may consist of, or consist essentially of, about 75% to about 95% by weight of kappa-carrageenans and about 5% to about 25% by weight of iota-carrageenans. In some embodiments of the present invention, the carrageenan mixture may consist essentially of about 75% to about 90% by weight of kappa-carrageenans and about 10% to about 25% by weight of iota-carrageenans. In some embodiments, the polysaccharide stabilizer of the gum texture modifier is kappa-carrageenan. In some embodiments, the polysaccharide stabilizer is a sulfated galactose-based polysaccharide polymer having a chemical structure comprising repeating units of $[C_{24}H_{36}O_{25}S_2^{-2}]$ and having a molecular weight of about 788.647 g/mol plus or minus 5% per repeating unit.

In some embodiments, the gum texture modifier contains about 0.50 to 12.0% of the polysaccharide stabilizer. In some embodiments, the gum texture modifier contains about 0.5% of the polysaccharide stabilizer, or about 1.0%, about 1.5%, about 2.0%, about 2.5%, about 3.0%, about 3.5%, about 4.0%, about 4.5%, about 5.0%, about 5.5%, about 6.0%, about 6.5%, about 7.0%, about 7.5%, or about 8.0% of the polysaccharide stabilizer. In some embodiments, the gum texture modifier contains about 0.65 to 10.0% of the polysaccharide stabilizer, or about 0.75 to 9.5%, about 0.85 to 9.0%, about 1.0 to 8.6%, about 1.4 to 8.2%, about 1.8 to 7.8%, about 2.3 to 7.4%, about 2.7 to 6.8%, about 3.0 to 6.3%, about 3.3 to 5.8%, about 3.8 to 5.2%, or about 4.6 to 5.0% of the polysaccharide stabilizer. In some embodiments, the gum texture modifier contains about 2.8 to 6.0% of the polysaccharide stabilizer. In some embodiments, the gum texture modifier contains about 3.0 to 5.55% of the polysaccharide stabilizer. In some embodiments, the gum texture modifier contains about 4.2 to 5.2% of the polysaccharide stabilizer.

Glyceryl stearate (IUPAC name: "octadecanoic acid, reaction products with 1,2,3-propanetriol (1:1), neutralized"), sometimes referred to as glycerol stearate, is the esterification product of plant-derived glycerol and stearic acid, a fatty acid obtained from palm kernel, vegetable, or soy oil. Glyceryl stearate is also available commercially as glyceryl stearate SE, the self-emulsifying grade of glyceryl stearate ("GMS SE"). Glyceryl stearate SE typically contains some sodium stearate and/or potassium stearate in amounts ranging from about 2% to about 8%. Glyceryl stearate and GMS SE are both plant-derived emulsifiers and dispersing agents. With the polysaccharide stabilizer and polysaccharide thickener of the gum texture modifier, glyceryl stearate or GMS SE imparts additional stability and strengthens the gel matrix structure of the gel texturizer base. In some embodiments, glyceryl stearate is used in the gum texture modifier. In some embodiments, glyceryl stearate SE is used in the gum texture modifier. Glyceryl stearate SE for use in the gum texture modifier is commercially available and can be purchased from, for example, BASF Care Solutions LLC (Florham Park, NJ), Stéarinerie Dubois (Boulogne-Billancourt, France), Croda International Plc. (Snaith, France), and Berg & Schmidt America LLC (Libertyville, IL).

In some embodiments, the gum texture modifier contains about 18.0 to 34.0% glyceryl stearate. In some embodiments, the gum texture modifier contains about 20.5% glyceryl stearate, or about 21.0%, about 21.5%, about 22.0%, about 22.5%, about 23.0%, about 23.5%, about 24.0%, about 24.5%, about 25.0%, about 25.5%, about 26.0%, about 26.5%, about 27.0%, about 27.5%, or about 28.0% glyceryl stearate. In some embodiments, the gum texture modifier contains about 20.0 to 30.0% glyceryl stearate, or about 20.3 to 29.5%, about 20.6 to 29.0%, about 21.0 to 28.6%, about 21.4 to 28.2%, about 21.8 to 27.8%, about 22.3 to 7.4%, about 22.7 to 26.8%, about 23.0 to 26.3%, about 23.3 to 25.8%, about 23.8 to 25.2%, or about 24.1 to 24.7% glyceryl stearate. In some embodiments, the gum texture modifier contains about 21.5 to 28.0% glyceryl stearate. In some embodiments, the gum texture modifier contains about 23.0 to 26.85% glyceryl stearate. In some embodiments, the gum texture modifier contains about 23.5 to 25.5% glyceryl stearate.

In some embodiments, the gum texture modifier contains about 18.0 to 34% glyceryl stearate SE. In some embodiments, the gum texture modifier contains about 20.5% glyceryl stearate SE, or about 21.0%, about 21.5%, about 22.0%, about 22.5%, about 23.0%, about 23.5%, about 24.0%, about 24.5%, about 25.0%, about 25.5%, about 26.0%, about 26.5%, about 27.0%, about 27.5%, or about 28.0% glyceryl stearate SE. In some embodiments, the gum texture modifier contains about 20.0 to 30.0% glyceryl stearate SE, or about 20.3 to 29.5%, about 20.6 to 29.0%, about 21.0 to 28.6%, about 21.4 to 28.2%, about 21.8 to 27.8%, about 22.3 to 7.4%, about 22.7 to 26.8%, about 23.0 to 26.3%, about 23.3 to 25.8%, about 23.8 to 25.2%, or about 24.1 to 24.7% glyceryl stearate SE. In some embodiments, the gum texture modifier contains about 21.5 to 28.0% glyceryl stearate SE. In some embodiments, the gum texture modifier contains about 23.0 to 25.55% glyceryl stearate SE. In some embodiments, the gum texture modifier contains about 24.0 to about 25.0% glyceryl stearate SE.

In some embodiments, the gum texture modifier of the gel texturizer base comprises clay in the amount of about 30.0 to 70.0%, the polysaccharide thickener in the amount of about 10.0 to 32.0%, the polysaccharide stabilizer in the amount of about 0.50 to 12.0%, and glyceryl stearate in the amount of about 18.0 to 34.0%. In some embodiments, the gum texture modifier of the gel texturizer base comprises clay in the amount of about 38.0 to 62.0%, the polysaccharide thickener in the amount of about 16.2 to 31.5%, the polysaccharide stabilizer in the amount of about 1.4 to 8.2%, and glyceryl stearate in the amount of about 20.0 to 30.0%. In some embodiments, the gum texture modifier of the gel texturizer base comprises clay in the amount of about 44.5 to 53.0%, the polysaccharide thickener in the amount of about 19.5 to 25.0%, the polysaccharide stabilizer in the amount of about 2.8 to 6.0%, and glyceryl stearate in the amount of about 21.5 to 28.0%. In some embodiments, the gum texture modifier of the gel texturizer base comprises clay in the amount of about 46.0 to 51.0%, the polysaccharide thickener in the amount of about 20.0 to 24.0%, the polysaccharide stabilizer in the amount of about 3.0 to 5.55%, and glyceryl stearate in the amount of about 23.0 to 26.85%. In some embodiments, the gum texture modifier of the gel texturizer base comprises clay in the amount of about 47.5 to 50.0%, the polysaccharide thickener in the amount of about 21.0 to 23.0%, the polysaccharide stabilizer in the amount of about 4.2 to 5.2%, and glyceryl stearate in the amount of about 23.5 to 25.5%.

In some embodiments, the gum texture modifier of the gel texturizer base comprises clay in the amount of about 30.0 to 70.0%, the polysaccharide thickener in the amount of about 10.0 to 32.0%, the polysaccharide stabilizer in the amount of about 0.50 to 12.0%, and glyceryl stearate SE in the amount of about 18.0 to 34.0%. In some embodiments, the gum texture modifier of the gel texturizer base comprises clay in the amount of about 38.0 to 62.0%, the polysaccharide thickener in the amount of about 16.2 to 31.5%, the polysaccharide stabilizer in the amount of about 1.4 to 8.2%, and glyceryl stearate SE in the amount of about 20.0 to 30.0%. In some embodiments, the gum texture modifier of the gel texturizer base comprises clay in the amount of about 44.5 to 53.0%, the polysaccharide thickener in the amount of about 19.5 to 25.0%, the polysaccharide stabilizer in the amount of about 2.8 to 6.0%, and glyceryl stearate SE in the amount of about 21.5 to 28.0%. In some embodiments, the gum texture modifier of the gel texturizer base comprises clay in the amount of about 46.0 to 51.0%, the polysaccharide thickener in the amount of about 20.0 to 24.0%, the polysaccharide stabilizer in the amount of about 3.0 to 5.55%, and glyceryl stearate SE in the amount of about 23.0 to 26.85%. In some embodiments, the gum texture modifier of the gel texturizer base comprises clay in the amount of about 47.5 to 50.0%, the polysaccharide thickener in the amount of about 21.0 to 23.0%, the polysaccharide stabilizer in the amount of about 4.2 to 5.2%, and glyceryl stearate SE in the amount of about 23.5 to 25.5%.

IV. GEL TEXTURIZER BASE FORMULATIONS

The gel texturizer base of the instant invention is a particular type of disperse system, sometimes referred to as a "hydrolipid dispersion," in which the lipophilic internal phase (i.e., the texture enhancer) is dispersed throughout the hydrophilic continuous phase (i.e., the solvent). Typically, hydrolipid dispersions contain a relatively low amount of the lipophilic phase (e.g., 2-20%) compared to the amount of the hydrophilic phase (e.g., 80-98%). Such hydrolipid dispersion systems are thermodynamically unstable, and are typically stabilized by the addition of suitable large polymers, such as, for example, acrylates/C10-30alkyl acrylate crosspolymers, hydroxypropyl methylcellulose, or polyacrylate. The addition of the large polymers, which are hydrated lyophilic colloids in the aqueous phase, form mono- to multilamellar films at the interfaces between the hydrophilic continuous phase and the lipophilic internal phase, thus stabilizing the dispersion. In the case of the instant invention, synthetic polymers, emulsifiers, and surfactants conventionally used to stabilize hydrolipid dispersions (i.e., the gel texturizer base) have been replaced with the gum texture modifier, which is comprised of natural and non-synthetic constituents that are considered to be less irritating to the skin.

The gel texturizer base for cosmetic products includes suitable amounts of a solvent, a texture enhancer, and a gum texture modifier, as described herein. Each component of the gel texturizer base, as described above, when combined together in the suitable amounts provides the gel texturizer base with the proper gel-like texture, consistency, viscosity, etc. for skin applications. When incorporated in a cosmetic product, the gel texturizer base acts as a vehicle for an even application and uniform delivery of the additional active ingredients of said cosmetic product, while providing the cosmetic product with desirable sensory properties (i.e., quick skin absorption, silky touch, not sticky, easily spreadable).

In some embodiments, the gel texturizer base comprises about 87.0 to 97.0% of the solvent. In some embodiments, the gel texturizer base comprises about 87.5% of the solvent, or about 88.0%, about 88.5%, about 89.0%, about 89.5%, about 90.0%, about 90.5%, about 91.0%, about 91.5%, about 92.0%, about 92.5%, about 93.0%, about 93.5%, about 94.0%, about 94.5%, about 95.0%, about 95.5%, or about 96.0% of the solvent. In some embodiments, the gel texturizer base comprises about 87.5 to 96.5% of the solvent, or about 88.0 to 96.0%, about 88.5 to 95.5%, about 88.8 to 95.0%, about 89.0 to 94.5%, about 89.2 to 94.0%, about 89.5 to 93.6%, about 89.8 to 93.3%, about 90.0 to 93.0%, about 90.3 to 92.8%, about 90.5 to 92.5%, about 90.8 to 92.2%, about 91.0 to 92.0%, about 91.2 to 92.5%, about 91.5 to 91.0%, about 91.0 to 91.5%, about 90.5 to 91.8%, or about 90.0 to 91.6% of the solvent. In some embodiments, the gel texturizer base comprises about 89.0 to 94.0% of the solvent. In some embodiments, the gel texturizer base comprises about 90.0 to 93.0% of the solvent. In some embodiments, the gel texturizer base comprises about 91.0 to 92.0% of the solvent.

In some embodiments, the gel texturizer base comprises about 1.0 to 6.0% of the texture enhancer. In some embodiments, the gel texturizer base comprises about 0.75% of the texture enhancer, or about 1.0%, about 1.5%, about 2.0%, about 2.3%, about 2.5%, about 2.6%, about 2.7%, about 2.8%, about 2.9%, about 3.0%, about 3.3%, about 3.5%, about 3.7%, about 4.0%, about 4.3%, about 4.5%, about 4.7%, about 5.0%, about 5.3%, about 5.5%, or about 5.8% of the texture enhancer. In some embodiments, the gel texturizer base comprises about 1.0 to 6.0% of the texture enhancer, or about 1.2 to 5.8%, about 1.3 to 5.6%, about 1.5 to 5.5%, about 1.8 to 5.2%, about 2.0 to 5.0%, about 2.2 to 4.8%, about 2.3 to 4.6%, about 2.5 to 4.5%, about 2.8 to 4.2%, about 3.0 to 4.0%, about 2.0 to 4.0%, about 2.3 to 3.8%, about 2.5 to 3.5%, about 2.6 to 3.3%, about 2.7 to 3.0%, or about 2.8 to 2.9% of the texture enhancer. In some embodiments, the gel texturizer base comprises about 2.0 to 5.0% of the texture enhancer. In some embodiments, the gel texturizer base comprises about 2.2 to 4.5% of the texture enhancer. In some embodiments, the gel texturizer base comprises about 2.4 to 4.0% of the texture enhancer.

In some embodiments, the gel texturizer base comprises about 2.0 to 8.0% of the gum texture modifier. In some embodiments, the gel texturizer base comprises about 3.0% of the gum texture modifier, or about 3.5%, about 4.0%, about 4.5%, about 5.0%, about 5.2%, about 5.3%, about 5.4%, about 5.5%, about 5.6%, about 5.7%, about 5.8%, about 5.9%, about 6.0%, about 6.4%, about 6.6%, about 6.8%, about 7.0%, about 7.3%, or about 7.5% of the gum texture modifier. In some embodiments, the gel texturizer base comprises about 3.5 to 7.5% of the gum texture modifier, or about 3.8 to 6.0%, about 4.0 to 6.8%, about 4.2 to 7.2%, about 4.4 to 7.0%, about 4.6 to 6.8%, about 4.8 to 6.6%, about 5.0 to 6.4%, about 5.2 to 6.2%, about 5.4 to 6.0%, about 5.5 to 5.8%, or about 5.6 to 5.7% of the gum texture modifier. In some embodiments, the gel texturizer base comprises about 4.0 to 6.5% of the gum texture modifier. In some embodiments, the gel texturizer base comprises about 4.5 to 6.0% of the gum texture modifier. In some embodiments, the gel texturizer base comprises about 5.0 to 6.0% of the gum texture modifier.

The weight to weight ratio of the texture enhancer to the gum texture modifier of the gel texturizer base of the invention will range from 0.25 to 1.0. For example, a gel texturizer base containing 91.5% of the plant juice solvent can also have 3.5% of the texture enhancer, and 6.0% of gum texture modifier. Thus, the weight to weight ratio of the texture enhancer to the gum texture modifier is 0.58 (i.e., 3.5:6.0=0.58). In some embodiments, the weight to weight ratio of the texture enhancer to the gum texture modifier of the gel texturizer base can be about 0.28, 0.30, 0.32, 0.35, 0.38, 0.40, 0.43, 0.46, 0.48, 0.50, 0.51, 0.52, 0.53, 0.54, 0.55, 0.56, 0.57, 0.58, 0.59, 0.60, 0.62, 0.64, 0.65, 0.66, 0.68, 0.70, 0.72, 0.74, 0.75, 0.76, 0.78, 0.80, 0.82, 0.84, 0.85, 0.86, 0.88, 0.90, 0.92, 0.95, 0.98, or about 1.0. In some embodiments, the weight to weight ratio of the texture enhancer to the gum texture modifier of the gel texturizer base ranges from 0.30 to 0.98, or from 0.35 to 0.95, 0.38 to 0.88, 0.40 to 0.85, 0.42 to 0.82, 0.44 to 0.78, 0.45 to 0.75, 0.46 to 0.73, 0.48 to 0.70, 0.45 to 0.68, 0.48 to 0.66, 0.50 to 0.65, 0.52 to 0.64, 0.53 to 0.63, 0.54 to 0.62, 0.55 to 0.61, 0.56 to 0.60, 0.50 to 0.53, 0.51 to 0.52, 0.50 to 0.51, 0.52 to 0.53, 0.51 to 0.53, or from 0.50 to 0.52. In some embodiments, the weight to weight ratio of the texture enhancer to the gum texture modifier of the gel texturizer base ranges from 0.35 to 0.75. In some embodiments, the weight to weight ratio of the texture enhancer to the gum texture modifier of the gel texturizer base ranges from 0.45 to 0.65. In some embodiments, the weight to weight ratio of the texture enhancer to the gum texture modifier of the gel texturizer base ranges from 0.50 to 0.60.

The combined weight percent of the texture enhancer and the gum texture modifier in the gel texturizer base compositions of the invention must not exceed 13.0% of the total weight of the gel texturizer base. In some embodiments, the combined weight percent of the texture enhancer and the gum texture modifier in the gel texturizer base compositions of the invention ranges from about 3.0 to 13.0% of the total weight of the gel texturizer base. In some embodiments, the combined weight percent of the texture enhancer and the gum texture modifier in the gel texturizer base is about 3.5% total weight of the gel texturizer base, or about 4.0%, about 4.5%, about 5.0%, about 5.5%, about 6.0%, about 6.5%, about 7.0%, about 7.5%, about 8.0%, about 8.5%, about 9.0%, about 9.5%, about 10.0%, about 10.5%, about 11.0%, about 11.5%, about 12.0%, about 12.5%, or about 13.0% of the total weight of the gel texturizer base. In some embodiments, the combined weight percent of the texture enhancer and the gum texture modifier in the gel texturizer base ranges from about 4.0 to 12.5% of the total weight of the gel texturizer base, or from about 4.5 to 12.4%, or about 5.0 to 12.2%, about 5.2 to 12.0%, about 5.4 to 11.8%, about 5.6 to 11.6%, about 5.8 to 11.4%, about 6.0 to 11.2%, about 6.2 to 11.0%, about 6.4 to 10.7%, about 6.6 to 10.5%, about 6.8 to 10.2%, about 7.0 to 10.0%, about 7.2 to 9.8%, about 7.4 to 9.6%, about 7.6 to 9.4%, about 7.8 to 9.2%, about 8.0 to 9.0%, about 6.0 to 12.0%, about 6.4 to 11.8%, about 6.8 to 11.5%, about 7.0 to 11.0%, about 7.0 to 10.5%, about 7.0 to 10.0%, about 7.5 to 9.5%, about 7.8 to 10.2%, about 8.0 to 10.4%, about 8.0 to 10.5%, about 8.0 to 10.0%, about 8.2 to 9.8%, about 8.4 to 9.4%, about 8.2 to 8.8%, or from about 8.4 to 8.6% of the total weight of the gel texturizer base. In some embodiments, the combined weight percent of the texture enhancer and the gum texture modifier in the gel texturizer base ranges from about 6.0 to 12.0% of the total weight of the gel texturizer base. In some embodiments, the combined weight percent of the texture enhancer and the gum texture modifier in the gel texturizer base ranges from about 7.0 to 11.0% of the total weight of the gel texturizer base. In some embodiments, the combined weight percent of the texture enhancer and the gum texture modifier in the gel texturizer base ranges from about 7.5 to 10.5% of the total weight of the gel texturizer base.

In some embodiments, the gel texturizer base for cosmetic products comprises the solvent in the amount of about 87.0 to 97.0%, the texture enhancer in the amount of about 1.0 to 6.0%, and the gum texture modifier in the amount of about 2.0 to 8.0%. In some embodiments, the gel texturizer base for cosmetic products comprises the solvent in the amount of about 88.0 to 96.0%, the texture enhancer in the amount of about 1.5 to 5.5%, and the gum texture modifier in the amount of about 3.5 to 7.5%. In some embodiments, the gel texturizer base for cosmetic products comprises the solvent in the amount of about 89.0 to 94.0%, the texture enhancer in the amount of about 2.0 to 5.0%, and the gum texture modifier in the amount of about 4.0 to 6.5%. In some embodiments, the gel texturizer base for cosmetic products comprises the solvent in the amount of about 90.0 to 93.0%, the texture enhancer in the amount of about 2.2 to 4.5%, and the gum texture modifier in the amount of about 4.5 to 6.0%. In some embodiments, the gel texturizer base for cosmetic products comprises the solvent in the amount of about 91.0 to 92.0%, the texture enhancer in the amount of about 2.4 to 4.0%, and the gum texture modifier in the amount of about 5.0 to 6.0%.

The gel texturizer bases of the invention can be prepared using customary methods and equipment known by those of skill in the art for preparing skin care products and cosmetics. The components of the gel texturizer base may be physically combined together in any order to achieve the weight percent compositions described herein. For example, the plant juice solvent, texture enhancer, and gum texture modifier can be combined together in any order as two or more separate distinct phases. Alternatively, the components of the plant juice solvent, texture enhancer, and gum texture modifier can be combined together in any order as two or more separate distinct phases. For example, the following components of the gel texturizer base may be physically combined together in any order to achieve the weight percent compositions described herein: plant juice derived supernatant, coconut alkanes, coco-caprylate/caprate, biosilicate fermentation product, polysaccharide conditioner, clay, polysaccharide thickener, polysaccharide stabilizer, and glyceryl stearate. In some embodiments, the plant juice solvent is physically combined with the gum texture modifier, or components thereof, and the texture enhancer, or components thereof, in any order to achieve the weight percent compositions described herein.

In some embodiments, the components of the gel texturizer base are physically combined together in any suitable number of phases to achieve the weight percent compositions. For example, phase A can be homogenously combined with phase B, wherein phase A is the plant juice solvent and phase B is a homogeneous mixture of the texture enhancer and the gum texture modifier. Alternatively, phase A can be homogenously combined with phase B first before introducing Phase C, wherein phase A is the plant juice solvent; phase B is either the gum texture modifier or the texture enhancer; and phase C is either the gum texture modifier or the texture enhancer, whichever was not used as phase B. As another non-limiting example in which phase A and phase B are homogenously combined first before introducing phase C, phase A is the plant juice solvent; phase B is one or more components of the gum texture modifier and the texture enhancer; and phase C is the remaining components of the gum texture modifier and/or the texture enhancer.

The components of the gel texturizer base are homogenously combined by stirring together the ingredients using sufficient agitation to achieve relative homogeneity of the hydrolipid dispersion. Agitation may be achieved, for example, using a standard propeller mixer, at a slow, moderate or even vigorous speed. The mixture can be uniformly interconnected, dispersed, and homogenized using conventional equipment such as a homogenizer, colloidal mill, line mixer, sonolator, combination mixer, propeller mixer, Turello mixer, or homogenizer-mixer. In this procedure, after coarse and fine dispersion in an emulsifier, such as a homogenizer, colloidal mill, or line mixer, subsequent fine dispersion may be performed in a high speed propeller mixer.

The temperature at which the mixtures are homogenized depends on the order in which each ingredient or phase is combined with one another. For example, mixtures are typically homogenized at a temperature of from about 5 to 80° C., about 5 to 75° C., about 5 to 70° C., about 5 to 65° C., about 5 to 60° C., about 5 to 55° C., about 5 to 50° C., about 5 to 45° C., about 5 to 40° C., about 5 to 35° C., about 5 to 30° C., about 5 to 25° C., about 5 to 20° C., or any ranges or fractional values between these. In some embodiments, the components of the plant juice solvent are mixed together at a temperature of from about 60 to 80° C. to form phase A. In some embodiments, one or more components of the gum texture modifier and the texture enhancer are mixed, or homogenized, together at a temperature of from about 5 to 70° C. to form phase B. In some embodiments, phase A, comprising the plant juice solvent, and phase B, comprising the homogenous mixture of one or more components of the gum texture modifier and the texture enhancer, are homogenized together at a temperature of from about 5 to 70° C. In some embodiments, phase C, comprising the remaining components of the gum texture modifier and/or the texture enhancer, and the homogenized mixture of phases A and B, comprising the plant juice solvent and one or more components of the gum texture modifier and the texture enhance, are homogenized together at a temperature of from about 20 to 50° C. to form the gel texturizer base of the invention.

The homogenization time depends on many factors, including the type of plant juice, the compositions of the texture enhancer and the gum texture modifier, any additional inactive ingredients (e.g., fragrance, pigments, opacifying agents, and/or pearlescing agent), the additional active ingredients (described below), the order in which each ingredient or phase is combined with one another, temperature, and type of equipment used to homogenize the mixture. The mixture is typically homogenized for a period of time sufficient to completely disperse the ingredients of one phase together with and throughout the ingredients of another phase to form a fully dispersed mixture. For example, mixtures are typically homogenized for a period of from about 5 to 60 min., about 5 to 55 min., about 5 to 50 min., about 5 to 45 min., about 5 to 40 min., about 5 to 35 min., about 5 to 30 min., about 5 to 25 min., about 5 to 20 min., about 5 to 15 min., about 5 to 10 min., or any ranges or fractional values between these.

In some embodiments, the components of the plant juice solvent are mixed together for about 5 to 60 min. to form phase A. In some embodiments, one or more components of the gum texture modifier and the texture enhancer are mixed, or homogenized, together for about 5 to 60 min. to form phase B. In some embodiments, phase A, comprising the plant juice solvent, and phase B, comprising the homogenous mixture of one or more components of the gum texture modifier and the texture enhancer, are homogenized together for about 5 to 25 min. to form a hydrolipid dispersion. In some embodiments, phase C, comprising the remaining components of the gum texture modifier and/or the texture enhancer, and the homogenized mixture of phases A and B, comprising a hydrolipid dispersion of the plant juice solvent and one or more components of the gum texture modifier and the texture enhance, are homogenized together for about 5 to 60 min., thereby forming a fully interconnected and dispersed three-dimensional network of the solvent, texture enhancer, and gum texture modifier. In some embodiments, the mixture is homogenized until the gel texturizer base has the desired jelly-like consistency, texture, feel and finish. In some embodiments, the mixture of phases A, B, and C is homogenized for about 30 minutes before combining the then homogenized gel base with inactive ingredients or active ingredients of a cosmetic product composition.

In some embodiments, the gel texturizer base can be combined with a fragrance. In some embodiments, the fragrance is a fresh fragrance or a floral fragrance. In some embodiments, the fragrance composition will contain natural extracts, such as essential oils. The fragrance ingredients combined with the gels of the present invention are the conventional ones known in the art. Suitable fragrance compounds and compositions can be found in the art including U.S. Pat. No. 4,145,184, Brain and Cummins, issued Mar. 20, 1979; U.S. Pat. No. 4,209,417, Whyte, issued Jun. 24, 1980; U.S. Pat. No. 4,515,705, Moeddel, issued May 7, 1985; U.S. Pat. No. 4,152,272, Young, issued May 1, 1979; U.S. Pat. No. 5,378,468 Suffis et al., U.S. Pat. No. 5,081,000 Akimoto et al., issued Jan. 14, 1992; U.S. Pat. No. 4,994,266 Wells, issued Feb. 19, 1991; U.S. Pat. No. 4,524,018 Yemoto et al., issued Jun. 18, 1985; U.S. Pat. No. 3,849,326 Jaggers et al., issued Nov. 19, 1974; U.S. Pat. No. 3,779,932 Jaggers et al., issued Dec. 18, 1973; JP 07-179,328 published Jul. 18, 1995; JP 05-230496 published Sep. 7, 1993; WO 96/38528 published Dec. 5, 1996; WO 96/14827 published May 23, 1996; WO 95/04809 published Feb. 16, 1995; and WO 95/16660 published Jun. 22, 1995; all of said U.S. patents and U.S. references being incorporated herein by reference. In addition P. M. Muller, D Lamparsky *Perfumes Art, Science, & Technology* Blackie Academic & Professional, (New York, 1994) is included herein by reference.

In some embodiments, the fresh fragrance composition is derived from a blend of pure essential oils produced by and for Juice Beauty, Inc. located in California, 94901 and at the website www.juicebeauty.com. In some embodiments, the fresh fragrance composition used to combine with the gel texturizer base is a blend of any two or more of the following pure essential oils: basil oil, bay oil, bergamot oil, black pepper oil, cedarwood oil, chamomile oil, cinnamon oil, citronella oil, clary sage oil, eucalyptus oil, fenugreek oil, frankincense oil, geranium oil, ginger oil, grapefruit oil, jasmine oil, juniper oil, lavender oil, lemon oil, lemongrass oil, lime oil, mandarin oil, marjoram oil, may chang oil, melissa oil, myrrh oil, neem oil, neroli oil, orange peel oil, patchouli oil, peppermint oil, pine oil, rose oil, rosehip oil, rosemary oil, rosewood oil, sage oil, sandalwood oil, sassafras oil, spearmint oil, star anise oil, tangerine oil, tarragon oil, tea tree oil, thyme oil, and ylang-ylang oil. In some embodiments, the fresh fragrance composition used to combine with the gel texturizer base is a blend of any two or more of the following pure essential oils: may chang oil, ylang ylang oil, bergamot oil, frankincense oil, lavender oil, orange peel oil, juniper oil, and clary sage oil. In some embodiments, the fresh fragrance composition used to combine with the gel texturizer base is a blend of lavender oil, orange peel oil, juniper oil, and clary sage oil.

In some embodiments, the floral fragrance is a floral rose fragrance, comprising the following ingredients: ethyl pelargonate, ethyl vanillin, heliotropine, phenoxyethanol, Santalex® T, ethylene brassylate, isopropyl myristate, terpineol. In some embodiments, the floral fragrance is a floral jasmine fragrance comprising the following ingredients: benzyl acetate, dihydroisojasmonate, cis-hex-3-en-1-ol, isoamyl acetate, ethylene brassylate, Santalex® T, isopropyl myristate, undecalactone gamma. In other embodiments, the floral jasmine fragrance comprises benzyl acetate, heliotropine, cis-hex-3-en-1-ol, ethylene brassylate, phenoxyethanol, Santalex® T, isopropyl myristate, undecalactone gamma.

In some embodiments, the fragrance is a unique blend of essential oils and aromatic extracts (i.e., a combination of a fresh fragrance and a floral fragrance), which are commercially available and known in the art. Such fragrances can be purchased from, for example, Carrubba, Inc. (Milford, CT), Givaudan S.A. (Vernier, Switzerland), International Flavors & Fragrances, Inc. (New York City, NY), or The Lebermuth Company (South Bend, IN).

V. ACTIVE INGREDIENTS

The gel texturizer bases of the invention can be used in combination with a variety of active ingredients to form various cosmetic products. The active ingredients that are combined with the gel texturizer base will depend on the intended use of the cosmetic product and its function (e.g., moisturizer, anti-wrinkle, eye treatment, mask, cleanser, acne treatment, etc.). Non-limiting examples of cosmetic products that can include the gel texturizer base of the invention include moisturizing compositions, eye treatment compositions, and facial mask compositions. Each of these products contain active ingredients as described below.

Moisturizing Composition

Moisturizing compositions are a product applied to skin to increase hydration (occlusivity), comfort, and lubrication. The moisturizing compositions will contain emollient ingredients. The CTFA (Cosmetic, Toiletry, and Fragrance Association) defines "emollient" as a cosmetic ingredient which helps to maintain the soft smooth, and pliable appearance of the skin; emollients function by their ability to remain on the skin surface or in stratum corneum to act as a lubricant, to reduce flaking, and to improve the skin's appearance. In some embodiments, the moisturizing compositions control the hydration state of the skin by forming an occlusive layer on the skin, keeping water inside the upper stratum corneum layers and consequently acting as moisturizers. Exemplary active ingredients of the moisturizing compositions include, but are not limited to, caprylic/capric triglycerides, cyclomethicone, dimethicone, glycols (e.g., hexylene glycol, pentylene glycol, butylene glycol, and propylene glycol), hyaluronic acid, fragrance, polymers, and peptides. In some embodiments, the moisturizing compositions comprise at least one of the following active ingredients (i.e., moisturizer active ingredients): caprylic/capric triglycerides, cyclomethicone, dimethicone, glycols (e.g., hexylene glycol, pentylene glycol, butylene glycol, and propylene glycol), hyaluronic acid, fragrance, polymers, and peptides.

In some embodiments, the cosmetic product is a moisturizing composition comprising a combination of the gel texturizer base of the invention and moisturizer active ingredients, wherein the amount of the gel texturizer base can range from about 5.0 to about 90.0% of the total weight of the moisturizing composition. In some embodiments, the amount of the gel texturizer base of a moisturizing composition cosmetic product can range from about 10.0 to about 88.0% of the total weight of the moisturizing composition, or from about 20.0 to about 85.0%, or from about 35.0 to about 80.0%, or from about 50.0 to about 78.0% of the total weight of the moisturizing composition cosmetic product. In some embodiments, the amount of the gel texturizer base of a moisturizing composition cosmetic product can range from about 65.0 to about 75.0% of the total weight of the moisturizing composition.

In some embodiments, the moisturizing composition comprising the gel texturizer base of the invention comprises about 40.0 to about 85.0% solvent, about 0.5 to about 5.0% texture enhancer, and about 0.5 to about 7.0% gum texture modifier. In some embodiments, the moisturizing composition comprising the gel texturizer base of the invention comprises about 50.0 to about 80.0% solvent, about 0.75 to about 4.5% texture enhancer, and about 1.0 to about 6.0% gum texture modifier. In some embodiments, the moisturizing composition comprising the gel texturizer base of the invention comprises about 55.0 to about 78.0% solvent, about 1.0 to about 4.0% texture enhancer, and about 1.5 to about 5.5% gum texture modifier. In some embodiments, the moisturizing composition comprising the gel texturizer base of the invention comprises about 60.0 to about 75.0% solvent, about 1.0 to about 3.5% texture enhancer, and about 1.8 to about 5.2% gum texture modifier. In some embodiments, the moisturizing composition comprising the gel texturizer base of the invention comprises about 60.0 to about 70.0% solvent, about 1.2 to about 3.0% texture enhancer, and about 2.0 to about 5.0% gum texture modifier.

Eye Treatment Compositions

The skin around the eyes is more fragile, more prone to dryness, and quicker to show age and fatigue. Squinting and constant movement of the eyes also hasten the appearance of lines and wrinkles, and fluids collect under the eyes and cause puffiness and dark circles. When applied to the skin around the eyes, eye treatment compositions can address some of these issues. Exemplary active ingredients of the eye treatment compositions include, but are not limited to, peptides, plant butters (e.g., shea butter, cocoa butter, liquid fractions of shea butter known under the INCI name *Butyrospermum parkii* (shea) butter), silicones (e.g., cyclomethicone, dimethicone, and non-volatile polymethylsiloxanes (PDMS)), PEGs (e.g., polyethylene glycols having an average molecular weight of from 100 to 300 and from 1000 to 9000), and other polymers (e.g., polyacrylic acid, hydroxypropyl cellulose, polyacrylamides, and polyquaternium-51). In some embodiments, the eye treatment compositions comprise at least one of the active ingredients (i.e., eye treatment active ingredients): peptides, plant butters (e.g., shea butter, cocoa butter, liquid fractions of shea butter known under the INCI name *Butyrospermum parkii* (shea) butter), silicones (e.g., cyclomethicone, dimethicone, and non-volatile polymethylsiloxanes (PDMS)), PEGs (e.g., polyethylene glycols having an average molecular weight of from 100 to 300 and from 1000 to 9000), and other polymers (e.g., polyacrylic acid, hydroxypropyl cellulose, polyacrylamides, and polyquaternium-51).

In some embodiments, the cosmetic product is an eye treatment composition comprising a combination of the gel texturizer base of the invention and eye treatment active ingredients, wherein the amount of the gel texturizer base can range from about 5.0 to about 94.0% of the total weight of the eye treatment composition. In some embodiments, the amount of the gel texturizer base of an eye treatment composition cosmetic product can range from about 15.0 to about 90.0% of the total weight of the eye treatment composition, or from about 35.0 to about 88.0%, or from about 50.0 to about 85.0%, or from about 60.0 to about 83.0% of the total weight of the eye treatment composition cosmetic product. In some embodiments, the amount of the gel texturizer base of an eye treatment composition cosmetic product can range from about 65.0 to about 80.0% of the total weight of the eye treatment composition.

In some embodiments, the eye treatment composition comprising the gel texturizer base of the invention comprises about 40.0 to about 90.0% solvent, about 0.5 to about 5.4% texture enhancer, and about 0.5 to about 7.5% gum texture modifier. In some embodiments, the eye treatment composition comprising the gel texturizer base of the invention comprises about 50.0 to about 85.0% solvent, about 0.75 to about 4.8% texture enhancer, and about 1.0 to about 6.5% gum texture modifier. In some embodiments, the eye treatment composition comprising the gel texturizer base of the invention comprises about 55.0 to about 80.0% solvent, about 1.0 to about 4.4% texture enhancer, and about 1.5 to about 5.8% gum texture modifier. In other embodiments, the eye treatment composition comprising the gel texturizer base of the invention comprises about 60.0 to about 78.0% solvent, about 1.0 to about 3.8% texture enhancer, and about 2.0 to about 5.6% gum texture modifier. In some embodiments, the eye treatment composition comprising the gel texturizer base of the invention comprises about 60.0 to about 75.0% solvent, about 1.2 to about 3.5% texture enhancer, and about 2.2 to about 5.4% gum texture modifier.

Facial Mask Compositions

A facial mask is intended to treat specific skin concerns, and typically only used 2-3 times a week as an additional step to daily skincare regimens. They are referred to as masks because the formulations are applied to the face in a thin layer and left on for some period of time. After a period of wearing the facial mask, in which the duration varies, the masks are removed by using water, a damp cloth or by peeling the solidified mask off. Purposes for using the facial mask compositions will vary. Depending on their ingredients, the facial mask compositions can tighten and tone, hydrate, cleanse, nourish, draw out impurities, calm and soothe, rejuvenate the skin, or any combination thereof. Other facial mask compositions improve specific skin issues such as acne scars or hyper-pigmentation.

Exemplary active ingredients of the facial mask compositions include, but are not limited to, but are not limited to, kaolin, glycerin, dimethicone, PEGs (e.g., polyethylene glycols having an average molecular weight of from 100 to 300 and from 1000 to 9000), polysorbate, plant extracts (e.g., aloe vera, basil, birch, burdock, comfrey, chamomile (including German chamomile), calendula, dandelion, echinacea, elderflower, green tea, fennel, horsetail, hyssop, lady's mantle, lavender, lemon balm, lime flower, linden, liquorice, marshmallow, nettle, Oregon grape, plantain, pomegranate, rose, rosemary, sage, St. John's wort, yarrow and witch hazel), and magnesium silicate. In some embodiments, the facial mask compositions comprise at least one of the following active ingredients (i.e., facial mask active ingredients): kaolin, glycerin, dimethicone, PEGs (e.g., polyethylene glycols having an average molecular weight of from 100 to 300 and from 1000 to 9000), polysorbate, plant extracts (e.g., aloe vera, basil, birch, burdock, comfrey, chamomile (including German chamomile), calendula, dandelion, echinacea, elderflower, green tea, fennel, horsetail, hyssop, lady's mantle, lavender, lemon balm, lime flower, linden, liquorice, marshmallow, nettle, Oregon grape, plantain, pomegranate, rose, rosemary, sage, St. John's wort, yarrow, and witch hazel), and magnesium silicate.

In some embodiments, the cosmetic product is a facial mask composition comprising a combination of the gel texturizer base of the invention and facial mask active ingredients, wherein the amount of the gel texturizer base can range from about 10.0 to about 98.0% of the total weight of the facial mask composition. In some embodiments, the amount of the gel texturizer base of a facial mask composition cosmetic product can range from about 15.0 to about 95.0% of the total weight of the facial mask composition, or from about 25.0 to about 94.0%, or from about 35.0 to about 93.0%, or from about 45.0 to about 90.0%, or from about 55.0 to about 88.0% of the total weight of the facial mask composition cosmetic product. In some embodiments, the amount of the gel texturizer base of a facial mask composition cosmetic product can range from about 60.0 to about 85.0% of the total weight of the facial mask composition.

In some embodiments, the facial mask composition comprising the gel texturizer base of the invention comprises about 45.0 to about 95.0% solvent, about 0.5 to about 5.8% texture enhancer, and about 1.0 to about 7.8% gum texture modifier. In some embodiments, the facial mask composition comprising the gel texturizer base of the invention comprises about 50.0 to about 90.0% solvent, about 0.75 to about 5.2% texture enhancer, and about 1.5 to about 7.2% gum texture modifier. In other embodiments, the facial mask treatment composition comprising the gel texturizer base of the invention comprises about 55.0 to about 88.0% solvent, about 1.0 to about 4.8% texture enhancer, and about 1.8 to about 6.2% gum texture modifier. In other embodiments, the facial mask treatment composition comprising the gel texturizer base of the invention comprises about 60.0 to about 85.0% solvent, about 1.2 to about 4.2% texture enhancer, and about 2.2 to about 5.8% gum texture modifier. In some embodiments, the facial mask composition comprising the gel texturizer base of the invention comprises about 60.0 to about 80.0% solvent, about 1.5 to about 3.8% texture enhancer, and about 2.5 to about 5.6% gum texture modifier.

Other active ingredients typically found in cosmetic products include plant oils (e.g., wheat germ, grapeseed, sesame, corn, apricot, castor, avocado, olive, soy bean, sweet almond, palm, rapeseed, cottonseed, hazelnut, macadamia, jojoba, alfalfa, poppy, pumpkin, rose, evening primrose, sunflower, and safflower oils), plant extracts such as rice and linseed extracts, vitamins such as Vitamin A, C, E, and B5, alpha- and beta-hydroxy acids, hyaluronic acid, and antioxidants such as tocopherols including alpha-, beta-, gamma- and delta-tocopherols.

VI. EVALUATION OF PROPERTIES

The gel texturizer base compositions of the invention will be tested for preferred physical and chemical properties. In some embodiments, the gel texturizer base composition is qualitatively assessed to determine its sensory aspects (e.g., gloss, integrity of shape, penetration force, compression force, stringiness, difficulty of spreading, absorbency, and stickiness). The viscosity, pH, and specific gravity of the gel texturizer base compositions are also evaluated. In some embodiments, the properties of the gel texturizer base can be evaluated before combining with active ingredients, after combining with active ingredients, or both before and after the addition of active ingredients. Commercial services, such as, for example, Avomeen Analytic Services (Ann Arbor, MI) and Bioscreen Testing Services, Inc. (Torrance, California), are available for evaluating the physical properties and chemical properties of the gel texturizer base compositions of the invention.

Sensory Evaluation

The gel texturizer base and cosmetic compositions containing the gel texturizer base of the instant invention will have the desired tactile properties and texture attributes. The gel texturizer base of the invention is pliable and has acceptable flow (shear-thinning). The gel texturizer base, and compositions thereof, form a soft, smooth film on the skin's surface. The texture of a cosmetically acceptable gel texturizer base and cosmetic product thereof will not have a texture that is waxy, tacky, heavy, or draggy. Rather, the texture of a cosmetically acceptable gel texturizer base and cosmetic composition product thereof will have a jelly-like, smooth, glossy and lightweight texture, permitting easy application to the skin and feathering. Sensorial analysis of the gel texturizer base and/or cosmetic compositions thereof can be performed using a descriptive test and reference scale to establish the sensory profile of gel texturizer base and/or cosmetic products thereof, as described in the publication "Impact of Polymers on Texture Properties of Cosmetic Emulsions: A Methodological Approach," Gilbert, L. et al, *Journal of Sensory Studies,* 2012, 27, pp. 392-402, the teaching of which is included herein by reference.

The sensory evaluation methods that can be used to discriminate and describe the gel texturizer base and/or cosmetic compositions thereof in terms of texture properties will take into account rheological principles and physical characteristics of the gel. For the purpose of the present invention, sensory evaluations of the gel texturizer bases and/or cosmetic compositions containing the gel texturizer base focus on the appearance and texture attributes of said gels and/or cosmetic compositions thereof. The conditions for the evaluations, such as, for example, environment, sample handling, and panelist skin conditioning, are to be carefully controlled by following the Standard Practice for Descriptive Skinfeel Analysis of Creams and Lotions given by the ASTM (ASTM Standard E1490 1992, 1997).

Texture attributes that can be used to evaluate and describe the gel texturizer base and/or cosmetic composition thereof include gloss, integrity of shape, penetration force, compression force, stringiness, difficulty spreading, absorbency, and stickiness. The sensory evaluation methods can be performed in phases in which particular texture attributes are analyzed. For example, gloss and integrity of shape can be evaluated in the appearance phase (i.e., phase 1); force of penetration, force of compression, and stringiness can be evaluated in the pick-up phase (i.e., phase 2); difficulty spreading and absorbance can be evaluated in the rub-out phase (i.e., phase 3); and stickiness can be evaluated in the residual appearance phase (i.e., phase 4). Prior to the evaluation of each texture attribute of phases 2 and 3, the evaluator will wash their hands and, in some cases, forearms using a hydroalcoholic gel cleanser. Gloss, integrity of shape, penetration force, compression force, difficulty spreading, and stickiness can be measured using a 0-9 scale with 0.5 increments and particular verbal descriptors. Stringiness can be measured in millimeters (e.g., length of filament string) and absorbency can be measured by the number of rubs necessary for the gel texturizer base and/or cosmetic composition thereof to penetrate the skin completely. See, Gilbert, L. et al, *Journal of Sensory Studies.*

The appearance phase of the sensory evaluation process can begin with analyzing the gloss attribute of the gel texturizer base and/or cosmetic composition containing the gel texturizer base. Gloss is defined as the amount of reflected light from the gel base or cosmetic product and is assessed in an evaluation box or booth in a suitable sensory laboratory. The gloss is evaluated by turning on a light in the box or booth and holding a 5 mL jar of the texturizer base or cosmetic composition 30 cm from the light source. The sample is tilted to catch the reflection, and the amount of gloss is evaluated. Gloss is evaluated using the 0-9 scale, with 0 indicating "matte" and 9 indicating "glossy." In some embodiments, the gel texturizer base composition of the instant invention will have a glossy appearance, with a sensory attribute score ranging from 6 to 9. Next, the integrity of shape of the gel texturizer base or cosmetic product is evaluated by dispensing about 5 g of the sample in a gentle spiral shape in a weight dish. Integrity of shape is defined as the degree to which the gel texturizer base or cosmetic product composition holds its given shape. During deposit and up to 10 seconds after, the sample's shape of evolution is evaluated, followed by assessing the integrity of shape: a score of 0 indicates that the deposit flattens and a score of 9 indicates that the deposit retains its shape (Gilbert, L. et al, *Journal of Sensory Studies*). In some embodiments, the gel texturizer base composition of the instant invention will retain its spiral shape up to 10 seconds after dispensing, with an integrity of shape sensory attribute score ranging from 6 to 9.

The pick-up phase of the sensory evaluation process involves evaluating the penetration force of the gel texturizer base and/or cosmetic composition containing the gel texturizer base. Penetration force is defined as the force required to penetrate forefinger into the gel base or cosmetic composition thereof. After washing hands with a hydroalcoholic gel, penetration force is analyzed by first placing a forefinger above the 5 mL jar containing the texturizer base or cosmetic composition, then, with closed eyes, plunging the forefinger slowly into the jar until the forefinger touches the bottom of the jar. The penetration force is evaluated using the 0-9 scale, with 0 indicating "soft" and 9 indicating "hard." In some embodiments, the gel texturizer base or cosmetic composition containing the gel texturizer base of the instant invention will have a moderately soft to slightly hard or firm penetration force, with a sensory attribute score ranging from 1 to 6. In other words, a jar containing the gel texturizer base and/or cosmetic composition thereof can be fully penetrated using a forefinger with a relatively soft force to slightly hard or firm force, while offering some resistance.

The next attribute to be assessed in the pick-up phase of the sensory evaluation process is compression force. Compression force is defined as the force required to fully compress the gel base and/or cosmetic composition thereof between thumb and forefinger. Compression force is analyzed by dispensing about 5 g of the sample on the tip of the thumb of washed hands, followed by compressing the dispensed sample slowly between the thumb and forefinger one time while keeping eyes closed. The compression force is evaluated using the 0-9 scale, with 0 indicating "soft" and 9 indicating "hard." In some embodiments, the gel texturizer base or cosmetic composition containing the gel texturizer base of the instant invention will have a moderately soft compression force, with a sensory attribute score ranging from 1 to 5. In other words, the gel base and/or cosmetic composition containing the gel base can be fully compressed between the thumb and forefinger using a soft force, while offering some resistance.

The final attribute to be assessed in the pick-up phase of the sensory evaluation process is stringiness. Stringiness is defined as the degree to which the gel texturizer base and/or cosmetic product thereof strings. About 5 g of the sample is dispensed on the tip of the thumb of washed hands. The thumb is placed horizontally at eye level, with a ruler placed vertically behind the thumb with the 0 mark at thumb level. The sample is compressed between the thumb and forefinger 10 times at a rate of 2 compressions per second. The maximum length of filament obtained in millimeters is the stringiness evaluation (Gilbert, L. et al, *Journal of Sensory Studies*). In some embodiments, the gel texturizer base or cosmetic product thereof, as described herein, will have low stringiness, with filament lengths ranging from 1 mm to 25 mm.

The rub-out phase of the sensory evaluation process can begin with an analysis of the difficulty of spreading the gel texturizer base and/or cosmetic composition containing the gel texturizer base. Difficulty of spreading is defined as the force required to move the product over the skin. After washing hands and forearms with a hydroalcoholic gel, a skin pen is used to make two lines on the inner surface of the forearm at 6 and 12 cm from the cook of the elbow. Then, about 5 g of the sample is dispensed on the first line 6 cm from the crook of the elbow, which is then spread from to the second line on the forearm (i.e., the line 12 cm from the crook of the elbow) using a finger-tipped push and adapting the force of the push necessary for the sample to reach the second line. Difficulty of spreading is evaluated using the 0-9 scale, with 0 indicating "soft" and 9 indicating "hard." In some embodiments, the gel texturizer base or the cosmetic composition thereof will require a low or soft force to move it across the skin, with a difficulty of spreading sensory attribute score ranging from 0 to 2. Absorbency is then evaluated, which is defined as the amount of time it takes for a product on the skin surface to completely lose its wetness and a high resistance to continue is perceived. After complete absorption, no more product is perceived on the skin surface. After washing hands and forearms with a hydroalcoholic gel, absorbency evaluations begin by making a 5 cm circle using a skin pen on the inner surface of the forearm at 6 cm from the crook of the elbow. About 5 g of sample is dispensed in the center of the circle, and the entire amount of the sample is spread within the circle in a circular motion at a rate of one and a half strokes per second using the forefinger. The spreading is ceased once the sample is completely absorbed into the skin (i.e., high slip resistance is perceived). Absorbency corresponds to the number of circles necessary to reach the cease point (Gilbert, L. et al, *Journal of Sensory Studies*). In some embodiments, the gel texturizer base and/or cosmetic composition thereof will be highly absorbent, requiring no more than 8 circles for complete absorption.

The residual appearance phase of the sensory evaluation process involves analyzing the stickiness of the gel texturizer base and/or cosmetic composition containing the gel texturizer base. Stickiness is defined as the degree to which the hand's edge adheres to the surface of the application site of the skin. Stickiness is evaluated immediately after evaluating the absorbency. The edge of the evaluator's hand will be strongly pressed over the application site of the absorbed sample, then slowly removed from the forearm. This is performed 3 times to determine stickiness. Stickiness is evaluated using the 0-9 scale, with 0 indicating "slightly" and 9 indicating "very" (Gilbert, L. et al, *Journal of Sensory Studies*). In some embodiments, the gel texturizer base and/or cosmetic composition thereof will be minimally sticky, with a stickiness sensory attribute score ranging from 0 to 3.

Viscosity

The gel texturizer bases of this invention are intended as a principle excipient of a variety of different low viscosity cosmetic products. In general, the viscosity of a material is a measure of its resistance to gradual deformation by shear stress or tensile stress. For liquids or gels, it corresponds to the informal concept of "thickness," for example, honey has a much higher viscosity than water. Viscosity is more commonly expressed, particularly in American Society for Testing Materials (ASTM) standards, as centipoise (cP). Centipoise is equal to the SI multiple millipascal seconds (mPa·s). For example, water at 20° C. has a viscosity of 1.002 mPa·s=1.002 cP.

Viscometers are used to measure the viscosity of a fluid or gel material under defined flow conditions and at given shear rates. They measure the drag caused by the interaction between the fluid and the object surface. The viscometer rotates a sensing tool in a material and measures the torque needed to overcome the viscous resistance to the induced movement, by driving the immersed tool (i.e., the spindle), through a beryllium copper spring. The degree to which the spring is wound is proportional to the viscosity of the fluid. For a material of given viscosity, the resistance will be greater as the spindle size and/or rotational speed increase. Viscosities of the gel texturizer base and/or cosmetic compositions containing the gel texturizer base can be determined using a conventional viscometer. For example, Brookfield Viscometers are the most common viscometers used in the cosmetic products and beauty industry to measure viscosity.

In some embodiments, the viscosity of the gel texturizer base is between about 5,000 and 500,000 cP. In some embodiments, the viscosity of the gel texturizer base is between about 5,000 and 450,000 cP, about 6,000 and 400,000 cP, about 7,000 and 350,000 cP, about 8,000 and 300,000 cP, about 9,000 and 250,000 cP, about 10,000 and 200,000 cP, about 11,000 and 150,000 cP, about 12,000 and 100,000 cP, about 14,000 and 95,000 cP, about 15,000 and 90,000 cP, about 16,000 and 85,000 cP, about 18,000 and 80,000 cP, about 20,000 and 75,000 cP, about 22,000 and 70,000 cP, about 24,000 and 65,000 cP, about 25,000 and 60,000 cP, about 26,000 and 55,000 cP, about 28,000 and 50,000 cP, about 30,000 and 45,000 cP, about 26,000 and 36,000 cP, about 28,000 and 35,000 cP, about 30,000 and 34,000 cP, about 32,000 and 35,000 cP, about 33,000 and 35,000 cP, or between about 33,500 and 34,500 cP. In some embodiments, the viscosity of the gel texturizer base is between about 10,000 and 100,000 cP. In some embodiments, the viscosity of the gel texturizer base is between about 12,000 and 90,000 cP. In some embodiments, the viscosity of the gel texturizer base is between about 15,000 and 85,000 cP. In some embodiments, the viscosity of the gel texturizer base is between about 20,000 and 75,000 cP. In some embodiments, the viscosity of the gel texturizer base is between about 25,000 and 50,000 cP.

In some embodiments, the viscosity of a cosmetic composition containing the gel texturizer base (i.e., moisturizing composition, eye treatment composition, and facial mask composition) is between about 1,000 and 800,000 cP. In some embodiments, the viscosity of a cosmetic composition containing the gel texturizer base is between about 5,000 and 750,000 cP, about 15,000 and 750,000 cP, about 25,00 and 700,000 cP, about 30,000 and 700,000 cP, about 40,000 and 650,000 cP, about 50,000 and 650,000 cP, about 60,000 and 600,000 cP, about 80,000 and 550,000 cP, or between about 100,000 and 500,000 cP. In some embodiments, the viscosity of a cosmetic composition containing the gel texturizer base is between about 150,000 and 750,000 cP. In some embodiments, the viscosity of a moisturizing composition containing the gel texturizer base is between about 180,000 and 600,000 cP. In some embodiments, the viscosity of a moisturizing composition containing the gel texturizer base is between about 200,000 and 500,000 cP. In some embodiments, the viscosity of a moisturizing composition containing the gel texturizer base is between about 230,000 and 450,000 cP. In some embodiments, the viscosity of an eye treatment composition containing the gel texturizer base is between about 200,000 and 650,000 cP. In some embodiments, the viscosity of a facial mask composition containing the gel texturizer base is between about 200,000 and 700,000 cP.

pH

The gel texturizer bases of this invention and the cosmetic compositions containing such gel texturizer bases will have a pH that is compatible with the optimal environment of the skin surface. The pH will also impart stability to and maintain the shelf life of the gel texturizer base and cosmetic compositions thereof. pH is by definition the negative log of the hydrogen ion concentration in solution (i.e., $pH=pKa+\log[A^-][HA]$) as set forth as set forth in the Henderson-Hasselbalch equation defining the relationship between pH and pKa. $[A^-]$ is the molar concentration of the salt (dissociated species) and HA is the concentration of the undissociated acid. When the concentrations of the salt and acid are equal, the pH of the system is equal to the pKa of the acid. The pKa is a dissociation constant determined by the strength of an acid or base. As used herein, pH refers to a measured pH value of the gel texturizer base and/or cosmetic compositions containing the gel texturizer base, and not to a calculated value requiring what may be complex determination of activities and measurement of very low concentrations. pH is generally measured using a digital pH meter or potentiometer apparatus.

The pH of the gel texturizer bases of this invention and the cosmetic compositions thereof will be in a range that is considered acceptable for avoiding the risk of irritation upon application to the skin. In other words, the pH of the gel texturizer bases and cosmetic compositions thereof will not be damaging to the skin, particularly the stratum corneum (SC), which is the top of the epidermis. The SC is a cornified layer of tightly packed flattened cells that acts as an outer skin covering resistant to physical damage and to prevent water loss from underlying layers. The underlying layers of the epidermis contain hydrolase enzymes and lipids that that make up the protective barrier layer and assist normal skin in regulating natural water loss in the SC. The constant renewal of the epidermal surface plays an important role in preventing moisture loss from the body and maintaining epidermal permeability barrier homeostasis (see, U.S. Patent Application Publication US 2005/0281853).

The skin epidermis generally exhibits a mild acidity with a pH of about 4.0 to about 6.4, with pH 5.0 appearing to be optimal for maintaining the lipid barrier (see, Mauro, T. Arch. Dermatol. Res. 1998, 290(4): 215-222; Katsuhiko Deguchi et al. Journal of Society of Cosmetic Chemists of Japan, Vol. 15, No. 2, p. 121-127, 1981). Most cosmetic products have a pH 6.5 to 8.0 in order to maintain stability and a shelf life up to at least two years. However, cosmetic products having a pH at around neutral or basic do not promote rebuilding of the skin's protective barrier, because the enzymes required for the rebuilding process have low activity at near neutral pH and only function well at a lower pH. On the other hand, acidic cosmetic products (e.g., pH 4.0 and below) will often cause burning or irritation to the skin and will typically have a shorter shelf life (see, U.S. Patent Application Publication US 2005/0281853). Therefore, the gel texturizer bases of the instant invention and cosmetic compositions thereof, are stable acidic cosmetic formulations that do not cause damage to the skin.

In some embodiments, the pH of the gel texturizer base is between about 1.0 and about 6.5. In some embodiments, the pH of the gel texturizer base is about 1.2, or about 1.4, about 1.6, about 1.8, about 2.0, about 2.2, about 2.4, about 2.6, about 2.8, about 3.0, about 3.2, about 3.4, about 3.6, about 3.8, about 4.0, about 4.2, about 4.4, about 4.6, about 4.8, about 5.0, about 5.2, about 5.4, about 5.6, about 5.8, about 6.0, about 6.2, or about 6.4. In some embodiments, the pH of the gel texturizer base is between about 1.0 and about 6.0, or about 1.5 and about 5.5, about 2.0 and about 5.0, about 2.5 and about 4.5, about 3.0 and about 4.0, about 3.0 and about 6.5, about 3.5 and about 6.0, about 4.0 and about 5.5, or between about 4.5 and about 5.5. In some embodiments, the pH of the gel texturizer base is between about 3.0 and about 6.5. In some embodiments, the pH of the gel texturizer base is between about 3.5 and about 6.0. In some embodiments, the pH of the gel texturizer base is between about 4.0 and about 5.5.

In some embodiments, the pH of a cosmetic composition containing the gel texturizer base (i.e., moisturizing composition, eye treatment composition, and facial mask composition) is between about 1.5 and about 8.0. In some embodiments, the pH of a cosmetic composition containing the gel texturizer base is between about 1.5 and about 7.5, about 2.0 and about 7.4, about 2.5 and about 7.2, about 3.0 and about 7.0, about 3.5 and about 6.9, about 4.0 and about 6.8, about 4.5 and about 6.7, about 4.8 and about 6.6, or between about 5.0 and about 6.5. In some embodiments, the pH of a cosmetic composition containing the gel texturizer base is between about 3.5 and about 7.5. In some embodiments, the pH of a moisturizing composition containing the gel texturizer base is between about 5.0 and about 6.5. In some embodiments, the pH of an eye treatment composition containing the gel texturizer base is between about 4.5 and about 6.9. In some embodiments, the pH of a facial mask composition containing the gel texturizer base is between about 3.5 and about 6.9.

SpG

The gel texturizer bases of this invention and the cosmetic compositions containing such gel texturizer bases have a density that invokes a light skin feel during and after applying to the skin surface without imparting a heavy, greasy film. The density will also be sufficient to maintain the gel matrix dispersion system. The density of the gel texturizer bases of this invention and the cosmetic compositions thereof will be expressed as specific gravity (SpG). SpG is by definition a density ratio of a substance in comparison to water at 4° C. and 1 atm. In other words, SpG refers to the density of a given substance divided by the density of water. The SpG of the gel texturizer bases and cosmetic compositions thereof can be measured with a suitable density or SpG determination apparatus. Techniques include: (i) pycnometer/weight per gallon cup, where the gel formulation at fixed temperatures is carefully introduced into a fixed-volume vessel of known volume and mass; and (ii) Electronic density/specific gravity meter, where a slow stream of the gel formulation at fixed temperatures is introduced into a flow-through cell and the density is determined by the oscillating body method. In some embodiments, the specific gravity is measured using a Cole Parmer specific gravity cup.

In some embodiments, the SpG at 25° C. of the gel texturizer base is at least about 0.75, in the range of about 0.75 to about 1.50, for example, about 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, 1.00, 1.05, 1.10, 1.15, 1.20, 1.25, 1.30, 1.35, 1.40, 1.45, or 1.50 at 25° C. In some embodiments, the SpG at 25° C. of the gel texturizer base is between about 0.85 and about 1.20, or about 0.90 and about 1.10, or between about 0.95 and about 1.00.

In some embodiments, the SpG at 25° C. of a cosmetic composition containing the gel texturizer base (i.e., moisturizing composition, eye treatment composition, and facial mask composition) is at least about 0.75, in the range of about 0.75 to about 1.80, for example, about 0.80, 0.90, 0.95, 1.0, 1.05, 1.10, 1.15, 1.20, 1.25, 1.30, 1.35, 1.40, 1.45, 1.50, 1.55, 1.60, 1.65, 1.70, 1.75 or 1.80 at 25 C. In some embodiments, the SpG at 25° C. of a cosmetic composition containing the gel texturizer base is between about 0.80 and about 1.60. In some embodiments, the SpG at 25° C. of a moisturizing composition containing the gel texturizer base is between about 0.99 and 1.10. In some embodiments, the SpG at 25° C. of an eye treatment composition containing the gel texturizer base is between about 0.79 and 1.20. In some embodiments, the SpG at 25° C. of a facial mask composition containing the gel texturizer base is between about 0.89 and 1.50.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

VII. EXAMPLES

The following examples are provided by way of illustration only and not by way of limitation. Those of skill will readily recognize a variety of noncritical parameters which could be changed or modified to yield essentially similar results.

Example 1. Synthesis of the Gel Texturizer Base

Gel texturizer bases of this invention were prepared by first obtaining organic aloe, apple, and grape juices for use as the solvent. The organic aloe, apple, and grape juices were purchased from the commercial sources as shown in Table 1 and prepared as described herein. The prepared organic aloe, apple, and grape juices shown in Table 1 were added to a main beaker and mixed until uniform at 70° C., forming phase A. Next, the coconut alkanes and coco-caprylate/caprate mixture of the texture enhancer (Table 2) and all the components of the gum texture modifier (Table 3; bentonite clay, xanthan gum, carrageenan, and glyceryl stearate SE) were mixed in a side beaker until uniform, forming phase B. Phase B was added directly to the main beaker containing phase A, vortex mixing using a high-speed propeller mixer at high speed for at least 15 minutes. The batch was cooled to 45° C. Phase C comprising the remaining components of the texture enhancer (Table 2; bamboo leaf ferment and biosaccharide gum) was added to the main beaker containing the homogenous mixture of phases A and B, and mixed until a homogenous mixture was formed. The mixing was reduced to low speed while the temperature of the gel texturizer base mixture was cooled to room temperature (i.e., between 20 and 25° C.).

TABLE 1

Solvent

| Ingredient | Source | Amount* |
|---|---|---|
| Organic aloe plant juice<br>pH: 3-5<br>APC: <100 CFU/g<br>Carb.: about 11.3% | Aloecorp, Inc.<br>(Tacoma, WA) | 50.0-60.0% |
| Organic apple juice<br>pH: 3.6<br>APC: <100 CFU/g<br>Carb.: about 11.2% | Local or national commercial source, such as, for example, Northwest Naturals, LLC (Bothell, WA) | 18.0-24.0% |
| Organic grape juice<br>pH: 4-5<br>APC: <100 CFU/g<br>Carb.: about 17.4% | Local or national commercial source, such as, for example, Old Orchard Brands, LLC (Sparta, MI) | 10.0-18.0% |

*The amount of each component is percentage of the component measured in weight per the total weight of the gel texturizer base

TABLE 2

Texture enhancer

| Ingredient | Source | Amount* |
|---|---|---|
| VEGELIGHT ® 1214 LC<br>Coconut alkanes<br>Coco-caprylate/caprate | Grant Industries, Inc.<br>(Elmwood Park, NJ) | - (1.5-4.5%)<br>- 1.0-4.0%<br>- 0.01-1.0% |
| Lactobacillus/<br>Arundinaria gigantea<br>leaf ferment filtrate | Local or national commercial source, such as, for example, Active Concepts, LLC (Lincolnton, NC) | 0.005-0.50% |
| Biosaccharide gum-1 | Solabia Group<br>(Pantin, France) | 0.005-0.50% |

*The amount of each component is percentage of the component measured in weight per the total weight of the gel texturizer base

TABLE 3

Gum texture modifier

| Ingredient | Source | Amount* |
|---|---|---|
| VANATURAL ®<br>Bentonite Clay | Vanderbilt Minerals, LLC (Norwalk, CT) | 1.5-4.5% |
| Xanthan gum, FCC | Spectrum Chemical Mfg. Corp. (New Brunswick, NJ) | 0.50-2.5% |

TABLE 3-continued

Gum texture modifier

| Ingredient | Source | Amount* |
|---|---|---|
| OLIGOGELINE ™ PF (carrageenan) | SEPPIC (Paris, France) | 0.01-1.2% |
| Cutina ® GMS SE (glyceryl stearate SE) | BASF Care Solutions LLC (Florham Park, NJ) | 0.50-2.5% |

*The amount of each component is percentage of the component measured in weight per the total weight of the gel texturizer base The gel texturizer base had the desired jelly-like consistency, stability, texture, feel and finish. The gel texturizer base was semi-transparent/opaque and off-white in color, with favorable spreadability characteristics (i.e., easily spreadable and glided across the skin surface). The gel texturizer base absorbed quickly into the skin without a sticky after-feel. The texture was smooth, glossy, and silky to the touch. The skin appeared brighter and having a reflectance, rather than dry and/or sticky.

Example 2. Gel Texturizer Base Formulation Ingredient Development

The following example demonstrates the development process of a cosmetic composition containing a gel texturizer base, in which the gel texturizer base ingredients that imparted the most desirable aesthetics and texture attributes upon the cosmetic composition were identified. Table 4 (below) shows the ingredient compositions for eight different gel texturizer base formulations within a cosmetic product, which were prepared as described in Example 1, followed by the addition of inactive and active ingredients of the cosmetic product composition and subsequent mixing. Each cosmetic composition containing the gel texturizer base formulation of Table 4 was qualitatively assessed to determine its sensory aspects (e.g., gloss, integrity of shape, compression force, stringiness, difficulty of spreading, absorbency, and stickiness). The results of the sensory analysis for each of the eight cosmetic compositions containing the gel texturizer base formulations are included in Table 4.

TABLE 4

Ingredient development: Sensory attributes of cosmetic compositions containing gel texturizer bases

| Exp. | Solvent | TE[a] | GTM[b] | Results* |
|---|---|---|---|---|
| 1 | aloe apple grape | bamboo ferment biosaccharide gum | Xanthan gum | Gloss - glossy (9/9)<br>Integrity of Shape - retains shape (8/9)<br>Compression Force - very soft (2/9)<br>Stringiness - not very stringy to very stringy (20-50 mm long)<br>Difficulty Spreading - easy to spread (1/9)<br>Absorbency - does not absorb well, 10-20+ circles<br>Stickiness - very sticky (9/9) |
| 2 | aloe apple grape | bamboo ferment biosaccharide gum | cellulose gum carrageenan *Ceratonia siliqua* gum sucrose | Gloss - glossy (9/9)<br>Integrity of Shape - does not retain shape (2/9)<br>Compression Force - almost liquid, viscosity dropped over time (1/9)<br>Stringiness - (20 mm)<br>Difficulty Spreading - easy to spread (1/9)<br>Absorbency - absorbs after 8 circles<br>Stickiness - sticky (8/9)<br>Notes: Lumpy texture, tacky and sticky dry down |
| 3 | aloe apple grape | Coconut alkanes coco-caprylate/caprate bamboo ferment biosaccharide gum | Xanthan gum bentonite glyceryl stearate SE | Gloss - semi glossy (6/9)<br>Integrity of Shape - (7/9)<br>Compression Force - soft (3/9)<br>Stringiness - less stringy (15-20 mm)<br>Difficulty Spreading - easy to spread (1/9)<br>Absorbency - absorbs well, 3-4 circles<br>Stickiness - stickiness increases after 1 minute (3/9-4/9)<br>Notes: Tightening effect, pills, sticky |
| 4 | aloe apple grape | Coconut alkanes coco-caprylate/caprate bamboo ferment biosaccharide gum | Bentonite hydroxyethylcellulose glyceryl stearate SE | Gloss - glossy (8/9)<br>Integrity of Shape - does not retain shape (2/9)<br>Compression Force - liquid (0/9)<br>Stringiness - too liquid to perform<br>Difficulty Spreading - easy to spread (1/9) |

TABLE 4-continued

Ingredient development: Sensory attributes of cosmetic compositions containing gel texturizer bases

| Exp. | Solvent | TE[a] | GTM[b] | Results* |
|---|---|---|---|---|
| 5 | aloe apple grape | Coconut alkanes coco-caprylate/caprate bamboo ferment biosaccharide gum | Potato starch modified Bentonite xanthan gum glyceryl stearate SE | Absorbency - absorbs well, 3 circles<br>Stickiness - stickiness dissipates (3/9)<br>Notes: Sticky, separation, low viscosity<br>Gloss - eggshell finish (4/9)<br>Integrity of Shape - retains shape (8/9)<br>Compression Force - soft (3/9)<br>Stringiness - not very stringy (10 mm)<br>Difficulty Spreading - spreads well (2/9) |
| 6 | aloe apple grape | Coconut alkanes coco-caprylate/caprate bamboo ferment biosaccharide gum | Bentonite potato starch modified xanthan gum carrageenan | Absorbency - fairly absorbent, 6 circles<br>Stickiness - sticky (5/9)<br>Notes: Good viscosity, sticky, does not absorb well<br>Gloss - glossy (8/9)<br>Integrity of Shape - does not fully retain shape/flattens (4/9)<br>Compression Force - very soft (2/9)<br>Stringiness - less stringy (20 mm)<br>Difficulty Spreading - easy to spread (1/9) |
| 7 | aloe apple grape | Coconut alkanes coco-caprylate/caprate bamboo ferment biosaccharide gum | Bentonite hydroxyethylcellulose carrageenan glyceryl stearate SE | Absorbency - absorbs better, 4 circles<br>Stickiness - sticky (5/9)<br>Gloss - glossy (8/9)<br>Integrity of Shape - very liquid (0/9)<br>Compression Force - very liquid (0/9)<br>Stringiness - very stringy (30 mm)<br>Difficulty Spreading - easy to spread (1/9)<br>Absorbency - moderate to difficult, sometimes soapy, 5 to 10+ circles<br>Stickiness - not too sticky (2/9), then stickiness increases (4/9)<br>Notes: Soapy application, low viscosity |
| 8 | aloe apple grape | Coconut alkanes coco-caprylate/caprate bamboo ferment biosaccharide gum | Bentonite xanthan gum carrageenan glyceryl stearate SE | Gloss - glossy (9/9)<br>Integrity of Shape - retains shape (8/9)<br>Compression Force - soft, but offers resistance (4/9)<br>Stringiness - not very stringy (20 mm)<br>Difficulty Spreading - easy to spread (1/9)<br>Absorbency - absorbs well, 3 circles<br>Stickiness - minimal stickiness (2/9)<br>Notes: Absorbs wells, not sticky, good viscosity<br>*Final formulation* |

[a]TE = texture enhancer;
[b]GTM = gum texture modifier;
*"Penetration force" was not assessed in these texture attribute studies.

The solvent was the same aloe/apple/grape juice mixture for formulations 1-8. The ingredients for the texture enhancer and gum texture modifier were adjusted in each formulation, as shown in Table 4. While formulations 1 and 2 were glossy in appearance, but did not absorb well and were too sticky. The ingredients of the texture enhancer were adjusted by adding coconut alkanes and coco-caprylate to the bamboo ferment and biosaccharide gum for formulations 3-8, while the gum texture modifier ingredients were varied for formulations 3-8 so as to identify the desired ingredient combination. As shown in Table 4, formulation 8 exhibited the best sensorial evaluation results compared the formulations 1-7, with the bentonite, xanthan gum, carrageenan, and glyceryl stearate SE selected as the ingredients of the gum texture modifier. Thus, the gel texturizer base of formula 8 was the final formulation.

Example 3. Optimization of Ingredient Amounts of Final Gel Texturizer Base Formulation The following example demonstrates the development of the optimized gel texturizer base of the instant invention. In this example, the ingredients of the final formulation identified in Example 2 (i.e., formula 8) were the same for each of the formulations shown below in Table 5 (experiments 1-6), but the amounts for the solvent, texture enhancer, gum texture modifier, and the ratio of texture enhancer to gum texture modifier were varied. Each of the gel texturizer base formulations of Table 5 were prepared according to the methods described in Example 1, and then qualitatively assessed to determine the sensory aspects for each formulation (e.g., gloss, integrity of shape, penetration force compression force, stringiness, difficulty of spreading, absorbency, and stickiness). The sensory analysis results for each of the six gel texturizer base formulations are included in Table 6. This is the procedure that was used to establish the amounts of the solvent, texture enhancer, gum texture modifier, and ratios thereof for the optimized gel texturizer base formulation.

TABLE 5

Amounts of ingredients used in the gel texturizer base

| Exp. | Solvent, % | TE, % | GTM, % | TE:GTM | pH | Viscosity, cP | SpG |
|---|---|---|---|---|---|---|---|
| 1 | 91.5 | 2.9 | 5.6 | 0.52 | 5.0 | 34,000 | 0.99 ± 0.01 |
| 2 | 93.0 | 2.0 | 5.0 | 0.40 | 5.0 | 30,000 | 0.99 ± 0.01 |
| 3 | 93.0 | 4.0 | 3.0 | 1.33 | 5.0 | water thin | 0.99 ± 0.01 |
| 4 | 97.0 | 2.0 | 1.0 | 2.00 | 5.5 | 1,000 | 0.99 ± 0.01 |
| 5 | 90.0 | 3.5 | 6.5 | 0.54 | 5.0 | 28,000 | 0.99 ± 0.01 |
| 6 | 95.0 | 2.5 | 2.5 | 1.00 | 5.0 | 15,000 | 0.99 ± 0.01 |

* The amount of each component is percentage of the component measured in weight per the total weight of the gel texturizer base

TABLE 6

Establishing criticality: Sensory attributes of gel texturizer bases

| Exp. | Solvent, % | TE, % | GTM, % | TE:GTM | Results |
|---|---|---|---|---|---|
| 1 | 91.5 | 2.9 | 5.6 | 0.52 | Gloss - glossy (9/9)<br>Integrity of Shape - retains shape (9/9)<br>Penetration Force - moderately soft (5/9)<br>Compression Force - very soft (2/9)<br>Stringiness - not stringy (1 mm long)<br>Difficulty Spreading - easy to spread (1/9)<br>Absorbency - absorbs well, 4 circles<br>Stickiness - absent (0/9) |
| 2 | 93.0 | 2.0 | 5.0 | 0.40 | Gloss - semi glossy (2/9)<br>Integrity of Shape - striations, but holds shape (8/9)<br>Penetration Force - (3/9)<br>Compression Force - (1/9)<br>Stringiness - (0 mm)<br>Difficulty Spreading - easy to spread (1/9)<br>Absorbency - absorbs after 8 circles<br>Stickiness - sticky (2/9) |
| 3 | 93.0 | 4.0 | 3.0 | 1.33 | Gloss - eggshell gloss (6/9)<br>Integrity of Shape - does not hold shape (0/9)<br>Penetration Force - (0/9)<br>Compression Force - very liquid (0/9)<br>Stringiness - too liquid to perform<br>Difficulty Spreading - easy to spread (5/9)<br>Absorbency - doesn't absorb well, sits on skin, 14-20 circles<br>Stickiness - (3/9)<br>Notes: separation, low viscosity |

TABLE 6-continued

Establishing criticality: Sensory attributes of gel texturizer bases

| Exp. | Solvent, % | TE, % | GTM, % | TE:GTM | Results |
|---|---|---|---|---|---|
| 4 | 97.0 | 2.0 | 1.0 | 2.00 | Gloss - eggshell gloss (8/9)<br>Integrity of Shape - does not hold shape (2/9)<br>Penetration Force - (1/9)<br>Compression Force - liquid (0/9)<br>Stringiness - 12 mm<br>Difficulty Spreading - easy to spread (1/9)<br>Absorbency - doesn't absorb well, sits on skin, 14-20 circles<br>Stickiness - fairly sticky (3/9) |
| 5 | 90.0 | 3.5 | 6.5 | 0.54 | Gloss - semi gloss (6/9)<br>Integrity of Shape - (7/9)<br>Penetration Force - (3/9)<br>Compression Force - soft (3/9)<br>Stringiness - not very stringy (4 mm)<br>Difficulty Spreading - spreads well (2/9)<br>Absorbency - absorbs fairly well, 6 to 7 circles<br>Stickiness - minimal stickiness (2/9) |
| 6 | 95.0 | 2.5 | 2.5 | 1.00 | Gloss - eggshell finish glossy (8/9)<br>Integrity of Shape - does not fully retain shape (4/9)<br>Penetration Force - soft (3/9)<br>Compression Force - very soft (2/9)<br>Stringiness - not stringy (2 mm)<br>Difficulty Spreading - easy to spread (1/9)<br>Absorbency - absorbs moderately well, 8-10 circles<br>Stickiness - sticky (5/9)<br>Notes: Sticky dry down, pilled |

As shown in Table 6, the results of the sensory analysis indicate that the amounts of solvent, texture enhancer, and gum texture modifier, and the ratio of texture enhancer to gum texture modifier for gel texturizer base formulation #1 was the optimized formulation, while formulations #2 and #5 had acceptable sensory results. This study highlights the importance of the amount of each component has on the final formula, and, more significantly, the impact the ratio of the texture enhancer to gum texture modifier has on the sensory attributes for the gel texturizer bases (TE:GTM =0.35 to 0.75).

Example 4. Comparative Study of Natural GTB and Synthetic GTB

The following example demonstrates the sensorial advantages of the non-petroleum based gel texturizer base of the instant invention as compared to a gel texturizer base containing synthetic petroleum based ingredients. Commercially available gel texturizer compositions, or components thereof, typically contain ingredients such as, for example, petrolatum, mineral oils, silicones, alcohol, polyacrylamide, water, silica, triethoxycaprylylsilane, polyethylene glycols, polyacrylic acid, sodium acrylates/C10-30 alkyl acrylate crosspolymer, aluminums, microcrystalline wax, and/or liquid paraffin. The ingredients of the synthetic gel texturizer base for this comparative study are shown in Table 7 below. The synthetic gel texturizer base contains the same juice solvent and texture enhancer of the gel texturizer base of the instant invention, but the gum texture modifier is synthetic and contains petroleum-derived ingredients: 45-70% polyacrylamide, 20-30% C13-14 isoparaffin, and 7% laureth-7 (SEPIGEL™ 305, SEPPIC, Fairfield, NJ). The ingredients and amounts thereof for the all-natural gel texturizer base are those described in Examples 1 and 3 (the optimized formulation).

The natural gel texturizer base formulation of Table 7 was prepared as discussed in Example 1. The synthetic gel texturizer base formulation of Table 7 was prepared by adding the synthetic gum texture modifier to the solvent, and mixing at moderate intensity until completely homogenized before mixing in the texture enhancer using a high-speed propeller mixer until arriving at a homogenous mixture. The natural and synthetic gel texturizer bases were qualitatively assessed to determine the sensory aspects (e.g., gloss, integrity of shape, penetration force compression force, stringiness, difficulty of spreading, absorbency, and stickiness). The sensory analysis results for the natural and synthetic gel texturizer base formulations are shown in Table 7.

TABLE 7

Natural GTB vs. synthetic petroleum based GTB test

| GTB | Solvent | TE | GTM | Results |
|---|---|---|---|---|
| Natural | 91.5% | 2.9% | 5.6% | Gloss - glossy (9/9) |
| | | | | Integrity of Shape - retains shape (9/9) |
| | | | | Penetration Force - moderately soft (5/9) |
| | | | | Compression Force - very soft (2/9) |
| | | | | Stringiness - not stringy (1 mm long) |
| | | | | Difficulty Spreading - easy to spread (1/9) |
| | | | | Absorbency - absorbs well, 4 circles |
| | | | | Stickiness - absent (0/9) |
| Synthetic | 91.5% | 2.9% | 5.6% Synthetic Alternate | Gloss - glossy (9/9) |
| | | | | Integrity of Shape - retains shape (9/9) |
| | | | | Penetration Force - moderately soft (5/9) |
| | | | | Compression Force - very soft (3/9) |
| | | | | Stringiness - not stringy (1 mm) |
| | | | | Difficulty Spreading - easy to spread (1/9) |
| | | | | Absorbency - absorbs well, 4 circles |
| | | | | Stickiness - absent (0/9) |

As shown in Table 7, the sensorial attributes of the all-natural gel texturizer base of the instant invention met the sensorial attributes of the gel texturizer base containing a synthetic gum texture modifier (Table 7).

What is claimed is:

1. A non-petroleum based gel texturizer base for cosmetic products comprising a solvent, a texture enhancer, and a gum texture modifier, wherein:
   a) the solvent is a plant juice derived supernatant having about 6.0 to about 20.0% carbohydrate content and an acidic pH of between about 2.2 and about 6.0, wherein the amount of the solvent ranges from about 89.0 to 94.0% of the total weight of the gel texturizer base;
   b) the texture enhancer is a mixture consisting essentially of about 87.0 to 92.0% coconut alkanes, about 4.0 to 6.5% coco-caprylate/caprate, about 0.5 to 3.5% bio-silicate fermentation product, and about 1.5 to 3.5% polysaccharide conditioner, wherein the amount of the texture enhancer ranges from about 2.0 to 5.0% of the total weight of the gel texturizer base; and
   c) the gum texture modifier is a mixture consisting essentially of about 44.5 to 53.0% clay, about 19.5 to 25.0% polysaccharide thickener, about 2.8 to 6.0% polysaccharide stabilizer, and about 21.5 to 28.0% glyceryl stearate, wherein the amount of the gum texture modifier ranges from about 4.0 to 6.5% of the total weight of the gel texturizer base;
   wherein the weight to weight ratio of the texture enhancer to the gum texture modifier of the gel texturizer base ranges from 0.35 to 0.75.

2. The gel texturizer base of claim 1, wherein the plant juice is selected from the group consisting of aloe juice, grape juice, lemon juice, apple juice, and mixtures thereof.

3. The gel texturizer base of claim 2, wherein the plant juice is a mixture consisting of aloe juice, grape juice, and apple juice.

4. The gel texturizer base of claim 1, wherein the solvent has a pH between about 3.0 and about 5.0.

5. The gel texturizer base of claim 1, wherein the coconut alkanes in the texture enhancer contain C12 alkanes in an amount that ranges from about 85.0 to about 90.0%.

6. The gel texturizer base of claim 1, wherein the weight to weight ratio of the bio-silicate fermentation product to the polysaccharide conditioner ranges from 0.45 to 1.5.

7. The gel texturizer base of claim 1, wherein the bio-silicate fermentation product is derived from leaves and stalks of bamboo.

8. The gel texturizer base of claim 1, wherein the polysaccharide conditioner is biosaccharide gum.

9. The gel texturizer base of claim 1, wherein the clay is smectite clay.

10. The gel texturizer base of claim 9, wherein the smectite clay is selected from the group consisting of montmorillonites, hectorites, bentonites, attapulgites, sepiolites, beidellites, saponites, and mixtures thereof.

11. The gel texturizer base of claim 1, wherein the polysaccharide thickener is xanthan gum.

12. The gel texturizer base of claim 1, wherein the polysaccharide stabilizer is a sulfated galactose-based polysaccharide.

13. The gel texturizer base of claim 12, wherein the sulfated galactose-based polysaccharide is carrageenan.

14. A composition comprising the gel texturizer base of claim 1 and a fragrance.

15. The composition of claim 14, wherein the fragrance is a blend of any two or more pure essential oils selected from the group consisting of may chang oil, ylang ylang oil, bergamot oil, frankincense oil, lavender oil, orange peel oil, juniper oil, and clary sage oil.

16. A moisturizing composition comprising the gel texturizer base of claim 1 and at least one compound selected from the group consisting of caprylic/capric triglyceride, cyclomethicone, dimethicone, glycols, hyaluronic acid, fragrance, polymers, and peptides.

17. The moisturizing composition of claim 16, wherein the composition has a pH between 5.0 and about 6.5.

18. The moisturizing composition of claim 16, wherein the composition has a viscosity between about 180,000 and 600,000 cP.

19. The moisturizing composition of claim 16, wherein the composition has a specific gravity between 0.99 to 1.1, wherein the specific gravity is a density ratio of the composition to water at 4° C. and 1 atm.

20. The moisturizing composition of claim 16, wherein the composition is a cosmetic product, and wherein the moisturizing composition comprises about 55.0 to about 78.0% of the solvent, about 1.0 to about 4.0% of the texture enhancer, and about 1.5 to about 5.5% of the gum texture modifier based on the total weight of the moisturizing composition.

21. An eye treatment composition comprising the gel texturizer base of claim 1 and at least one compound selected from the group consisting of peptides, plant butters, silicones, and polymers.

22. A facial mask composition comprising the gel texturizer base of claim 1 and at least one compound selected from the group consisting of kaolin, glycerin, dimethicone, PEGs, polysorbate, plant extracts, and magnesium silicate.

23. A composition comprising the gel texturizer base of claim 1 and sunflower seed oil.

24. A composition comprising the gel texturizer base of claim 1 and tocopherol.

25. A composition comprising the gel texturizer base of claim 1 and alpha-hydroxy acids, beta-hydroxy acids, or a combination thereof.

26. A method of manufacturing a non-petroleum based gel texturizer base for cosmetic products comprising: combining a solvent, a texture enhancer, and a gum texture modifier, wherein:
a) the solvent is a plant juice derived supernatant having about 6.0 to about 20.0% carbohydrate content and an acidic pH of between about 2.2 and about 6.0, wherein the amount of the solvent ranges from about 89.0 to 94.0% of the total weight of the gel texturizer base;
b) the texture enhancer is a mixture consisting essentially of about 87.0 to 92.0% coconut alkanes, about 4.0 to 6.5% coco-caprylate/caprate, about 0.5 to 3.5% bio-silicate fermentation product, and about 1.5 to 3.5% polysaccharide conditioner, wherein the amount of the texture enhancer ranges from about 2.0 to 5.0% of the total weight of the gel texturizer base; and
c) the gum texture modifier is a mixture consisting essentially of about 44.5 to 53.0% clay, about 19.5 to 25.0% polysaccharide thickener, about 2.8 to 6.0% polysaccharide stabilizer, and about 21.5 to 28.0% glyceryl stearate, wherein the amount of the gum texture modifier ranges from about 4.0 to 6.5% of the total weight of the gel texturizer base;
wherein the weight to weight ratio of the texture enhancer to the gum texture modifier of the gel texturizer base ranges from 0.35 to 0.75.

* * * * *